(12) United States Patent
Najafi et al.

(10) Patent No.: US 7,204,168 B2
(45) Date of Patent: Apr. 17, 2007

(54) HAND CONTROLLER AND WRIST DEVICE

(75) Inventors: Farshid Najafi, Winnipeg (CA); Nariman Sepehri, Winnipeg (CA)

(73) Assignee: The University of Manitoba, Winnipeg, Manitoba (CA)

( * ) Notice: Subject to any disclaimer, the term of this patent is extended or adjusted under 35 U.S.C. 154(b) by 626 days.

(21) Appl. No.: 10/785,115

(22) Filed: Feb. 25, 2004

(65) Prior Publication Data
US 2005/0183532 A1    Aug. 25, 2005

(51) Int. Cl.
*G05G 13/00* (2006.01)

(52) U.S. Cl. .............................. 74/471 XY; 74/490.12; 901/9

(58) Field of Classification Search ........... 74/471 XY, 74/490.12, 490.13, 491; 901/9, 3, 4
See application file for complete search history.

(56) References Cited

U.S. PATENT DOCUMENTS

| | | | |
|---|---|---|---|
| 4,555,960 A | 12/1985 | King | |
| 4,628,765 A | 12/1986 | Dien et al. | |
| 4,638,798 A | 1/1987 | Shelden et al. | |
| 4,686,866 A | 8/1987 | Rosheim | |
| 4,723,460 A | 2/1988 | Rosheim | |
| 5,305,653 A | 4/1994 | Ohtani et al. | |
| 5,397,323 A | 3/1995 | Taylor et al. | |
| 5,721,566 A | 2/1998 | Rosenberg et al. | |
| 5,805,140 A | 9/1998 | Rosenberg et al. | |
| 5,816,105 A | 10/1998 | Adelstein | |
| 5,824,007 A | 10/1998 | Faraz et al. | |
| 5,855,583 A | 1/1999 | Wang et al. | |
| 6,024,576 A | 2/2000 | Bevirt et al. | |
| 6,026,703 A | 2/2000 | Stanisic et al. | |
| 6,088,020 A | 7/2000 | Mor | |
| 6,095,011 A * | 8/2000 | Brog.ang.rdh | ........... 74/490.03 |
| 6,104,382 A | 8/2000 | Martin et al. | |
| 6,154,198 A | 11/2000 | Rosenberg | |
| 6,192,143 B1 | 2/2001 | Souluer | |

(Continued)

OTHER PUBLICATIONS

G.J. Hamlin, A.C. Sanderson, "A novel concentric multi-link spherical joint with parallel robotics applications", Proceedings IEEE International Conference on Robotics and Automation, pp. 1267-1272, 1994.

(Continued)

*Primary Examiner*—David M. Fenstermacher
(74) *Attorney, Agent, or Firm*—C. A. Rowley

(57) ABSTRACT

A compact four degrees of freedom parallel mechanism suitable for use as a hand control or wrist is provided that has backdrivability, is singularity free and has a large workspace and a large force reflecting capability. The structure is light but rigid, and the electric actuators are all placed on the ground or base and provide independent control of each degree of freedom. Each degree of freedom is connected to an actuator either directly or through a cable drive system. The first two degrees of freedom are created by two identical pantographs pivoted together on pivoted joints to define a hemispherical motion of an object (end point) about a center point (hemisphere center). The third and fourth degrees of freedom represent rotation and sliding motions of the object around and along the radius of the created hemisphere, respectively. The axes of these latter degrees of freedom are concentric, and these axes intersect with the axis of the pantographs pivoted joints at the hemispheric center.

20 Claims, 27 Drawing Sheets

U.S. PATENT DOCUMENTS

| | | | |
|---|---|---|---|
| 6,201,984 | B1 | 3/2001 | Funda et al. |
| 6,244,809 | B1 | 6/2001 | Wang et al. |
| 6,271,833 | B1 | 8/2001 | Rosenberg et al. |
| 6,336,374 | B1 * | 1/2002 | Brogardh et al. ........ 74/490.03 |
| 6,339,969 | B1 | 1/2002 | Salcudean et al. |
| 6,351,549 | B1 | 2/2002 | Souluer |
| 6,368,332 | B1 | 4/2002 | Salcudean et al. |
| 6,400,837 | B2 | 6/2002 | Souluer |
| 6,418,811 | B1 | 7/2002 | Rosheim |
| 6,425,865 | B1 | 7/2002 | Salcudean et al. |
| 6,429,849 | B1 | 8/2002 | An et al. |
| 7,127,962 | B2 * | 10/2006 | Angeles et al. .......... 74/490.05 |

OTHER PUBLICATIONS

V. Hayward, "Toward a seven axis haptic device", Proceedings IEEE International Conference on Intelligent Robots and Systems: Human Robot Interaction and Cooperative Robots, pp. 133-139, 1995.

R. Baumann, W. Maeder, D. Glauser, R. Claval, "The PantoScope: a spherical remote-center-of-motion parallel manipulator for force reflection", Proceedings IEEE International Conference on Robotics and Automation, pp. 718-723, 1997.

A. Faraz, Sh. Payendeh, "A robotic case study: optimal design for laparoscopic positioning stands", International Journal of Robotics Research, vol. 17, No. 9, pp. 986-995, 1998.

E. Degoulange, L. Urbain, P. Caron, S. Boudet, J.L. Megnien, F. Pierrot, E. Dombre., "HIPROCRATE: an intrinsically safe robot for medical applications", Proceedings IEEE/RSJ International Conference on Intellligent Robots and Systems, pp. 959-964, 1998.

A. Gourdon, Ph. Poignet, G. Poisson, P. Vieyres, P. Marche, "A new robotic mechanism for medical application", Proceedings IEEE/ASME International Conference on Advanced Intelligent Mechatronics, pp. 33-38, 1999.

A.J. Madhani, G. Niemeyer, K. Salisbury, "The Black Falcon: a teleoperated surgical instrument for minimally invasive surgery", Proceedings IEEE/RSJ International Conference on Intelligent Robots and Systems, pp. 936-944, 1998.

M.C. Cavusoglu, M.C. Tendick, S.Sh. Sastry, "A laparoscopic telesurgical workstation", IEEE Transactions on Robotics and Automation, vol. 15, No. 4, pp. 728-739, 1999.

P. Vischer, R. Clavel, "Argos: A novel 3-DoF parallel wrist mechanism", International Journal of Robotics Research, vol. 19, No. 1, pp. 5-11, 2000.

W.H. Zhu, S.E. Salcudean, S. Bachmann, P. Abolmaesumi, "Motion /force/image control of a diagnostic ultrasound robot", Proceedings IEEE International Conference on Robotics and Automation, pp. 1580-1585, 2000.

J.M. Wiitala, M.M. Stanisic, "Design of an overconstrained and dexterous spherical wrist", ASME Journal of Mechanical Design, vol. 122, pp. 347-353, 2000.

S.E. Salcudean, W.H. Zhu, P. Abolmaesumi, S. Bachmann, P.D. Lawrence, "A robot system for medical ultrasound", Proceedings 9th International Symposium of Robotics Research (ISSR'99), pp. 195-202, 2000.

J.H. Lee, K.S. Eom, B.J. Yi, I.H. Suh, "Design of a new 6 DOF parallel haptic device", Proceedings IEEE International Conference on Robotics and Automation, pp. 886-891, 2001.

M. Mitsubishi, Sh. Warisawa, T. Tsuda, T. Higuchi, N. Koizumi, H. Hashizume, K. Fujiwara, "Remote ultrasound diagnostic system", Proceedings IEEE International Conference on Robotics and Automation, pp. 1567-1574, 2001.

J. Yoon, J. Ryu, "Design, fabrication, and evaluation of a new haptic device using a parallel mechanism", IEEE/ASME Transactions on Mechatronics, vol. 6, No. 3, pp. 221-230, 2001.

K. Masuda, E. Kimura, N. Tateishi, K. Ishihara, "Three dimensional motion mechanism of ultrasound probe and its application for tele-echography system", Proceedings IEEE/RSJ International Conference on Intelligent Robots and Systems, pp. 1112-1116, 2001.

Ch. Duriez, D. Lamy, Ch. Chaillou, "A parallel manipulator as a haptic interface solution for amniocentesis simulation", Proceedings IEEE International Workshop on Robot and Human Interactive Communication, pp. 176-181, 2001.

C. Delgorge et al., "OTELO project: Mobile Tele-Echography using an ultra-light robot", Telemed'02, 2002, London, UK.

L. Birglen, C. Gosselin, N. Pouliot, A new three DoF haptic device, IEEE Transactions on Robotics and Automation, vol. 18, No. 2, pp. 166-175, 2002.

N.S. Guerin, L. Bassit, G. Poisson, C. Delgorge, Ph. Arbeille, P. Vieyres, "Clinical validation of a mobile patient-expert tele-echography system using ISDN lines", Proceedings IEEE-EMBS Information Technology Applications in Biomedicine, pp. 24-26, 2003.

A.V. Gonzales, et al., "TER: A system for robotic tele-echography", Proceedings International Conference of Medical Image Computing and Computer-Assisted Intervention, pp. 326-334, 2001.

* cited by examiner

HAND CONTROLLER AND WRIST DEVICE

FIELD OF INVENTION

The present invention relates to a three or four Degree of Freedom (DoF) structure that may be used as a hand controller or haptic to be manipulated (preferably with force feedback) and/or a wrist structure the movement of which is to be controlled.

BACKGROUND OF THE PRESENT INVENTION

The concept of remote control in the medical field for diagnosis and or other operations to be performed by a Doctor on a remote patient is gaining more and more acceptance as it may be used to overcome serious problems of availability particularly in areas of low population insufficient to support locally a doctor having specific expertise. For Example, accurate assessment of abdomen and interpretation of abdominal pain are difficult, particularly for the inexperienced clinician or nurse. Errors and uncertainty can lead to delays in diagnosis and even death, as in appendicitis. These difficulties are amplified for remote patients who may have less timely and unequal access to expert clinical care. Although there is considerable interest and research in palpation technique in telehealth applications, currently there is no system equipped with kinematically similar configurations hand controller and robotic wrist that permits distant clinical palpation. This includes abdominal examination as well as ultrasound diagnosis, which require expert assessment and are a frequent cause of patient transfer.

Haptic controllers and wrists of many different forms have been proposed and used in controlling wrist that may but need not be of similar construction.

With respect to the design of hand controllers or haptic devices for medical procedures, the haptic devices developed by Rosenberg et al. (see U.S. Pat. No. 5,721,5665, 805,140, 6,271,833) and Bevirt et al., U.S. Pat. No. 6,024,576, have all two degrees of freedom providing two rotations about a fixed point (also termed center-of-rotation). They all have simple parallel structures. Additional extra degrees of freedom to these devices will unusually enlarge them or will require the actuators not to be grounded (i.e., become non-floating). Similarly, the force feedback mechanisms by Martin et al., U.S. Pat. No. 6,104,382, and Rosenberg, U.S. Pat. No. 6,154,198, have only two degrees of freedom providing two rotations about a fixed point and use a parallel structure.

The three DoF parallel linkage by Adelstein, U.S. Pat. No. 5,816,105, provides three translational displacements of the end point. The haptic device by Mor, U.S. Pat. No. 6,088,020, has three active and two passive degrees of freedom. It does not have a fixed remote center-of-rotation. The adjustable surgical stand by Faraz et al., shown in U.S. Pat. No. 5,824,007, includes two separate pantographs each providing spherical motion about fixed points. It uses a serial linkage mechanism and the actuators are not grounded.

Birglen et al. in Birglen, L., Gosselin, C., Pouliot, N. (2002), "Shape, a new 3 DoF haptic device", IEEE Transactions on Robotics and Automation; 18(2) 166–175, reported the development of three degrees of freedom haptic device using a spherical parallel mechanism.

Duriez et al. in Duriez, Ch., Lamy, D., Chaillou, Ch. (2001), "A parallel manipulator as a haptic interface solution for amniocentesis simulation", proceedings IEEE International Workshop on Robot and Human Interactive Communication, describes the development of a parallel robot for simulating the terminal organ that moves on a spherical surface with variable radius.

The PantoScope by Baumann et al., in Baumann, R., Maeder, W., Glauser, D., Claval, R. (1997), "The Panto-Scope: a spherical remote center-of-motion parallel manipulator for force reflection", proceedings IEEE International Conference on Robotics and Automation, describes the use of two non-identical pantograph-like mechanisms to build a parallel, spherical, remote center-of-motion manipulator with force reflecting capabilities. The use of non-symmetrical pantographs, however, works against the uniformity requirement [see paper by Hayward, V. (1995), "Toward a seven axis haptic device", proceedings IEEE International Conference on Intelligent Robots and Systems], which may degrade the performance of the device.

The six degrees of freedom haptic devices by Lee et al. [see Lee, J. H., Eom, K. S., Yi, B. J., Suh, I. H. (2001), "Design of a new six Dof parallel haptic device", proceedings IEEE International Conference on Robotics and Automation], and Yoon and Ryu [see Yoon, J., Ryu, J. (2001), "Design, fabrication, and evaluation of a new haptic device using a parallel mechanism", IEEE/ASME Transactions on Mechatronics 6 (3): 221–230], use non-floating actuators, but to keep the remote center-of-motion at a prescribed location, all degrees of freedom need to be active.

U.S. Pat. Nos. 6,339,969 and 6,368,332 both to Salcudean et al., each discloses a device having several degrees of freedom each employing a plurality of pantographs to control the movement of an end point and one of which has been specifically designed for assisting a surgeon in performing.

With respect to the design of novel robotic wrists, Stanisic et al. in U.S. Pat. No. 6,026,703 and the paper Wiitala, J., Stanisic, M. M. (2000), "Design of an overconstrained and dexterous spherical wrist", ASME Journal of Mechanical Design. 122: 347–353, describe a wrist structure formed with a dexterous split equator joint device with all points of all links moving on spheres. Thus, there is no remote center-of-motion outside the mechanism.

Compact wrist actuators by Rosheim described in U.S. Pat. Nos. 4,686,866, 4,723,460 and 6,418,811 have three degrees of freedom with linear actuators. These devices provide spherical motion of an end point about a fixed point, which is inside the mechanism. The spherical robotic wrist by Dien et al., U.S. Pat. No. 4,628,765, consists of two perpendicular semi-circular yokes to provide a spherical motion, with no remote center-of-motion. The yokes can be heavy, need precision machining and usually exhibit backlash. The stereotactic apparatus for locating or removing lesions developed by Shelden et al. and described in U.S. Pat. No. 4,638,798, provides the required motions for ultrasounds and palpation. The actuators in this device, however, are floating (i.e., they are placed at the moving joints) making it bulky and heavy.

The wrist for detecting very small breast anomalies by Souluer, U.S. Pat. Nos. 6,192,143; 6,351,549; and 6,400,837, consists of a positioning device, fully adjustable bed and a detection head, which should work together to position/orient the probe over the breast for palpating. The device is not only big, but also cannot provide the required motion for ultrasound diagnosis.

Funda et al., U.S. Pat. No. 6,201,984, developed a remote center-of-motion device for endoscopic surgery. The device provides a spherical motion about a fixed point with two circular guides. Available circular guides are bulky, heavy and difficult to be machined precisely. The actuators are also floating, which would not fulfil the requirements of the wrist design for the purpose of the preferred applications of the present invention.

The remote center-of-motion robot for surgery by Taylor et al., U.S. Pat. No. 5,397,323, has four degrees of freedom and uses a serial linkage mechanism. All the actuators are mounted on the proximal part of the device (not on the ground) and located on the same plane as the work point. Thus, it is not easy to install this device on the implement of a manipulator. The Black Falcon instrument by Madhani et al. described in the paper by Madhani, A. J., Niemeyer, G., Salisbury, K. (1998), "The Black Falcon: a teleoperated surgical instrument for minimally invasive surgery", proceedings IEEE/RSJ International Conference on Intelligent Robots and Systems, and the Laparoscopic positioning manipulator described in Faraz, A. and Payandeh, Sh. (1998), "A robotic case study: optimal design for laparoscopic positioning stands", in International Journal of Robotics Research 17 (9): 986–995, have similar structures as the one belonging to Taylor et al. (see U.S. Pat. No. 5,397,323 referred to above).

The laproscopic workstation by Cavusoglu et al. described in Cavusoglu, M. C., Tendick, M. C., Sastry, S. Sh. (1999), "A laparoscopic telesurgical workstation", IEEE Transactions on Robotics and Automation 15 (4): 728–739, uses three linear actuators with grounded motors (but appear to be coupled) for the first three degrees of freedom and one floating actuator for the fourth degree of freedom.

The parallel mechanism by Vischer and Clavel described in Vischer, P., Clavel, R. (2000), "Argos: A novel 3-DoF parallel wrist mechanism", International Journal of Robotics Research 19 (1): 5–11, provides three degrees of freedom rotational motion about a fixed working point. However, the remote center-of-motion is enclosed within the mechanism at some configurations. The roll motion is also limited to 120 degrees.

The paper by Hamlin, G. J., Sanderson, A. C. (1994), "A novel concentric multilink spherical joint with parallel robotics applications", proceedings IEEE International Conference on Robotics and Automation, teaches the use of a pantograph mechanism to built novel spherical joints.

Degoulange et al. [see the paper by Degoulange, E., Urbain, L., Caron, P., Boudet, S., Megnien, J. L., Pierrot, F., Dombre. E. (1998), "HIPROCRATE: an intrinsically safe robot for medical applications", proceedings IEEE/RSJ International Conference on Intelligent Robots and Systems], reports a device for ultrasound diagnosis; however, all joints are in motion during the tasks. Similarly, Salcudean et al., U.S. Pat. No. 6,425,865 [see also the paper by Zhu, W. H., Salcudean, S. E., Bachmann, S., Abolmaesumi, P. (2000), "Motion /force/image control of a diagnostic ultrasound robot", proceedings IEEE International Conference on Robotics and Automation, and the paper by Salcudean, S. E., Zhu, W. H., Abolmaesumi, P., Bachmann, S., Lawrence, P. D. (2000), "A robot system for medical ultrasound", proceedings 9$^{th}$ International Symposium of Robotics Research (ISRR'99)], designed and constructed complete robots for moving ultrasonic probes on the patient's skin with a given force. Accurate palpating of the probe along the roll axis, however, can only be made by the rotation of the entire parallelogram linkage about two perpendicular axes of rotation, and translation of the entire robot over a table. Although the system is counterbalanced and backdrivable, motors are non-floating and the inertial effect of the system is not negligible.

The design by Masuda et al. as described in the paper by Masuda, K., Kimura, E., Tateishi, N., Ishihara, K. (2001), "Three dimensional motion mechanism of ultrasound probe and its application for tele-echography system", proceedings IEEE/RSJ International Conference on Intelligent Robots and Systems, requires the whole mechanism to sit on patient. As such the workspace is limited. Also, for orienting the probe about a fixed point on the attention skin, all joints need to move.

The wrist by Gourdon et al. described in Gourdon, A., Poignet, Ph., Poisson, G., Vieyres, P., Marche, P. (1999), "A new robotic mechanism for medical application", proceedings IEEE/ASME International Conference on Advanced Intelligent Mechatronics, uses gears that affects the back-drivability of the system and generates backlash and also have coupled degrees of freedom.

The European 'OTELO' project discussed in Guerin, N. S., Bassit, L., Poisson, G., Delgorge, C., Arbeille, Ph., Vieyres, P. (2003), "Clinical validation of mobile patient-expert tele-echography system using ISDN lines", Proceedings IEEE-EMBS Information Technology Applications in Biomedicine; also in Delgorge et al. (2002) "OTELO project: mObile Tele-Echography using an ultra-Light rObot", proceedings Telemed'02, describes the development of a four degree-of-freedom wrist with a remote center-of-motion. In their design, in order to produce a single pitch or yaw motion, two degrees of freedom must work cooperatively. Some of the motors are also floating. As a result, the conical workspace is limited. The wrist also has a singular configuration inside its workspace. The European 'TER' project described in Gonzales, A. V., et al. (2001). "TER: a system for robotic tele-echography", proceedings International Conference of Medical Image Computing and Computer Assisted Intervention, describes the development of a robotic tele-echography system that uses parallel configuration based on pneumatic artificial muscles. The system appears to be bulky with limited workspace. Furthermore, the device entirely embraces the patient and there is no reasonable access to the patient in emergency cases.

Mitsubishi et al. as described in Mitsubishi M., Warisawa, Sh., Tsuda, T., Higuchi, T., Koizumi, N., Hashizume, H., Fujiwara, K. (2001), "Remote ultrasound diagnostic system", proceedings International IEEE Conference on Robotics and Automation, have developed a telerobotic system consisting of circular guides connected in a serial configuration and embedded with gears of high ratios. The mechanism is heavy, large (it has a size of a human trunk) and is therefore not mobile. Also, it does not appear to be backdrivable due to the use of semi circular spur gears moved by small pinions.

BRIEF DESCRIPTION OF THE PRESENT INVENTION

It is the main object of the present invention to provide a four DoF structure that may function as a hand controller and/or as a wrist mechanism.

It is an object of the present invention to provide a telerobotic system that may be used for diagnosis and/or other operations to be performed by a doctor or physician on a remote patient. Preferred applications of the invention are in the areas of Distance Abdominal Palpation (DAP) and Distance Ultrasound Diagnosis (DUD). The DAP-DUD system will primarily be used in situations wherein a bedside expert is not available. This allows patients who would normally be transferred to the location of the specialist, to be examined by the specialist without having to travel. Thus, the services and information will be delivered to individuals in many cases without leaving their own communities.

It is a further objective of the present invention to provide an improved hand controller or haptic.

It is yet another objective to provide an improved wrist structure.

Preferred Form of Hand Controller

A desktop compact three or four degrees of freedom mechanism suitable for use as a hand control is provided that preferably has backdrivability, is singularity free and has a large workspace and a large force reflecting capability. The structure is light but rigid, and the actuators are all placed on the ground or base and provide independent control of each degree of freedom. Each degree of freedom is connected to an actuator either directly or through a cable drive system. The first two degrees of freedom are created by two identical pantographs pivoted together on pivoted joints to define a hemispherical motion of an object (end point) about a center point (hemisphere center). The third and fourth (if provided) degrees of freedom represent sliding and rotational motions, respectively, of the end point object along and around the radius of the hemisphere created by the first and second degrees of freedom. The axes of these latter (third and fourth) degrees of freedom are concentric, and these axes intersect with the axis of the pantographs pivoted joints at the hemispheric center.

The third degree of freedom preferably is obtained using a cable drive and a slider in combination with a ball spline shaft that converts the rotating motion of an inner universal joint into sliding movement of the object (end point) through a pair of decoupling ball bearings.

The fourth degree of freedom preferably is obtained using a tube in combination with the ball spline nut that transmits the rotational motion of an outer universal joint to the end point or object. Sliding behavior of the ball spline in combination with a ball bearing is used to decouple the third and fourth degrees of freedom from each other. Another ball bearing is used to decouple the rotational motion of the ball spline nut from the pantographs pivoted joint. The moving object (which in normal operation is held by the expert) is attached to the end of ball spline shaft and preferably is configured so that it can be held in two places while being manipulated.

Preferred Form of Wrist

The wrist may have up to four degrees of freedom. The first two degrees of freedom are created by two identical pantographs pivoted together to define a spherical motion of a probe about a fixed point i.e. a created hemisphere. The third degree of freedom can be either sliding along the radius of the created hemisphere or rotation around it, to define a roll motion. Or, the wrist may incorporate both sliding and rotation to provide four degrees of freedom. Different modules may be mounted on the wrist to provide the third, and/or third and fourth degrees of freedom of the wrist.

One module that provides sliding motion incorporates a telescopic double universal joint and accommodates the first two degrees of freedom. This construction can be used for palpating over an abdomen by pressing a probe or end point in a desired orientation. A second module may be used to perform both the roll (rotating) and sliding motion bringing the total number of degrees of freedom to four. This construction when used for applying ultrasound device allows a probe or end point such as an ultrasound device to be three-dimensionally oriented about the fixed point (center point) while being pressed on the patient's body similar to the standard hand movements of the clinical expert.

All degrees of freedom are kinematically decoupled and are controlled by actuators (electric motors) that are fixed to the base of the wrist and are located away from the patient.

The power from each actuator is preferably transmitted to the driven axis by cables allowing the mechanism to be backdrivable. This not only allows easy measurements of the output force at the actuator sides, but also allows the probe to be passively pushed back by the patient in emergency circumstances. The mechanism exhibits a singular free, low friction, zero backlash, compact, rigid motion with a high-sustained output force.

Broadly, the present invention relates to a hand controller or wrist device comprising a base and a moveable portion moveable relative to said base, said moveable portion having a main longitudinal axis and an end point, a pair of pantographs each formed by a plurality of pivotably interconnected links arranged for pivotal movement in a plane, said planes being mutually perpendicular, means for pivotably mounting each said pantograph adjacent to one of its ends for rotational movement on its pivotal axis relative to said base in a direction substantially perpendicular to its plane and coupling means connecting each of said pantographs adjacent to its end remote from its one end to move said end point in a hemispherical path about a center point when said pantographs are pivoted on their said means for pivotably mounting, said pantographs defining a first and a second degree of freedom of said end point;

said center point being defined by the intersection of said pivotal axes and said main longitudinal axis, an inner universal joint, said inner universal interconnecting a first inside element and a second inside element forming a pair of inside elements that define a third degree of freedom of said end point, said first of said inside elements including a pair of portions and means for translating axial movement substantially parallel to said main axis of one of said pair portions of said first inner element to rotational movement of a second portion of said pair of portions of said first inner element and vice versa while permitting relative rotational movement between said one and said second portions, said end point being connected to said one portion of said one of said second pair of elements and means for mounting said second inside element for rotation about it axis relative to said base;

said coupling means connecting said pantographs to said one portion while permitting movement of said one portion relative to said pantographs.

Preferably, said device further comprises an outside universal joint concentric with said inside universal joint combines with said inside universal joint to provide a pair of concentric universal joints, said outside universal joint interconnecting a first outside element and second outside element that form a pair of outside elements; and means coupling said first outside element to said one portion of said first inside element to prohibit relative rotational movement while permitting relative axial movement between said one portion and said first outside element.

Preferably, said pair of outside elements define a fourth degree of freedom of said end point.

Preferably, said device is a controller and said center point and said inner universal joint pivot point are in the same location.

Preferably, said device further comprises a separate actuator for each of said degrees of freedom and each said actuator is supported on said base.

Preferably, said device is a controller and said actuators provide force feedback to said end point in each of said degrees of freedom and said center point is defined by the intersection of said pivotal axes and said main longitudinal axis and said end point is moved about said center point by operation said degrees of freedom.

Preferably, said actuator for said third degree of freedom is coupled to said second inside element and through said inner universal joint to said second portion of said first inside element.

Preferably, said means for translating axial movement to rotational movement and vice versa include a belt type drive which includes a pulley formed by a pulley that rotates with said second portion and a belt having a path of travel parallel to said axial movement and connected to said one portion so that movement of said belt moves said one portion substantially axially.

Preferably, said actuator for said fourth degree of freedom includes a belt type drive coupling with said second outside element of said pair of outside elements and through said outside universal joint with said first outside element of said pair of outside elements. Preferably, said device is a wrist and said actuators drive said end point in each of said degrees of freedom.

Preferably, said means for mounting said second inside element for rotation about it axis includes a second inside universal joint, said second inside universal joint coupled on one side to said second inside element and its other side is rotatably mounted on said base. Preferably, a second outside universal joint concentric with said second inside universal joint combines with said second inside universal joint to provide a second pair of concentric universal joints, said second outside universal joint coupled on one side to said second outside element and its other side is rotatably mounted on said base.

Preferably, said actuator for each of said first and second degrees of freedom includes a belt type drive, drivingly interconnecting its respective said means for pivotably mounting with its actuator.

Preferably, said actuator for said third degree of freedom is coupled to one side of said second inside universal joint and another side of said second inner universal joint is connected to said second inside element and through said inner universal joint to said second portion of said first inside element.

Preferably, said actuator for said fourth degree of freedom includes a belt type drive coupling with one side of said first outside universal joint.

Preferably, said means for translating axial movement to rotational movement and vice versa includes a worm type gear.

Preferably, said one portion is a module.

BRIEF DESCRIPTION OF THE SEVERAL VIEWS OF THE DRAWINGS

Further features, objects and advantages will be evident from the following detailed description of the preferred embodiments of the present invention taken in conjunction with the accompanying drawings in which.

DETAILED DESCRIPTION OF THE INVENTION

Figure 1:
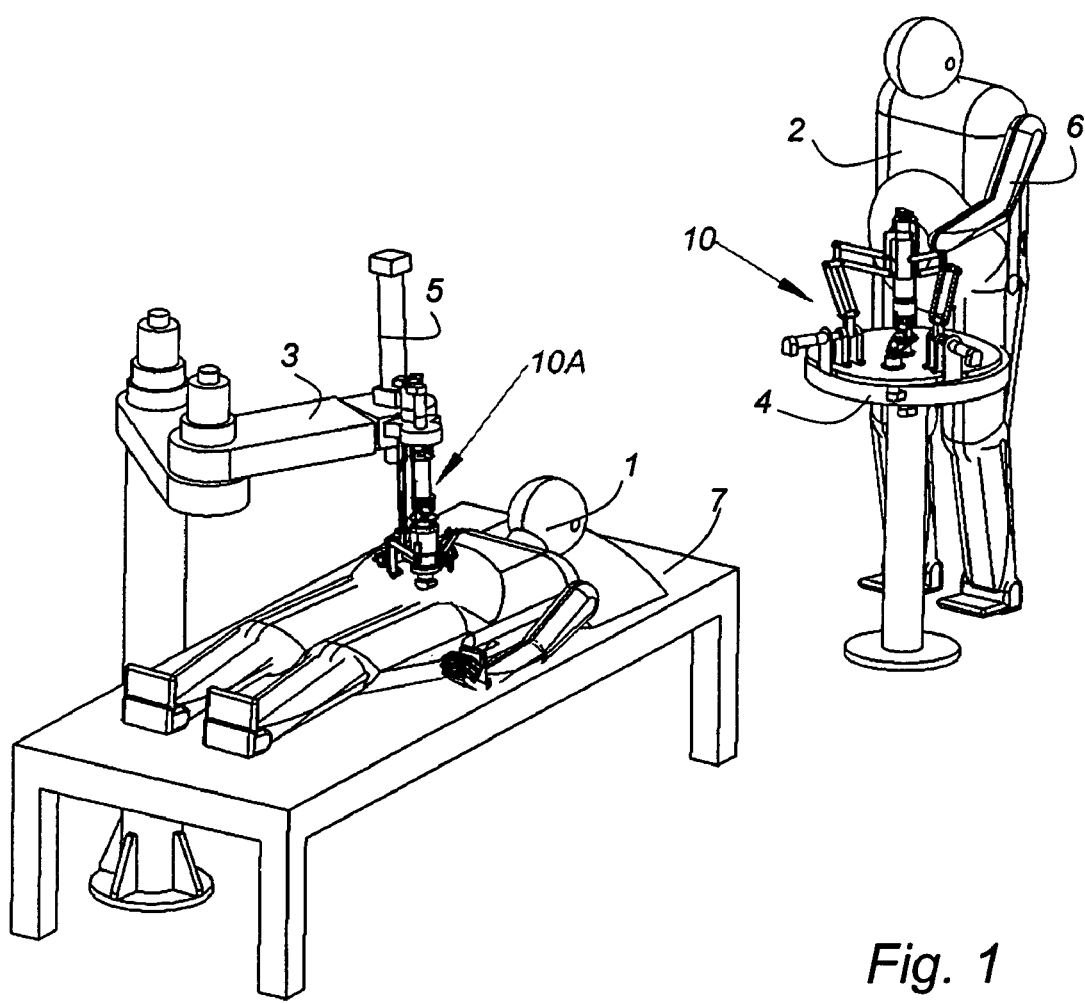
FIG. 1 is an isometric representation of the present invention showing the haptic (hand controller) and the wrist in different physical locations to illustrate control of the wrist from a location remote from the wrist.

The present invention has many applications including those in the area of telerobotic and ultrasound/palpation procedures for which it is particularly adapted. As indicated in FIG. 1 the patient 1 is positioned on an examining table 7 at a location remote from the expert (physician) 2 who maneuvers the haptic or controller 10 mounted on a suitable table or base 4. In the illustrated arrangement the physician is showing using only one arm 6, but it will be apparent that either arm or both arms may be used. The controller 10 is held by a clinical expert and provides three or four degrees of freedom for orienting and positioning the wrist 10A which is mounted on a platform 5 with prismatic motion which is positioned by a stand 3 in overlying relationship to the patient 1 lying on table 7 at the location remote from the expert 2. The hand controller 10 reflects the sensed forces applied against of from the patient 1 to the physician's 2 hand i.e. the hand controller is provided with force feedback in known manner. The invention thus may be used to improve health care in rural and urban sites, where distance is a critical factor.

Preferred Form of Hand Controller

The first embodiment of the present invention illustrated in FIGS. 2 through 11 inclusive and the second embodiment illustrated in FIGS. 12 through 27 are devices 10 (or 10A) that may function either as wrists or as controllers such has hand controller or joysticks.

Figure 2:
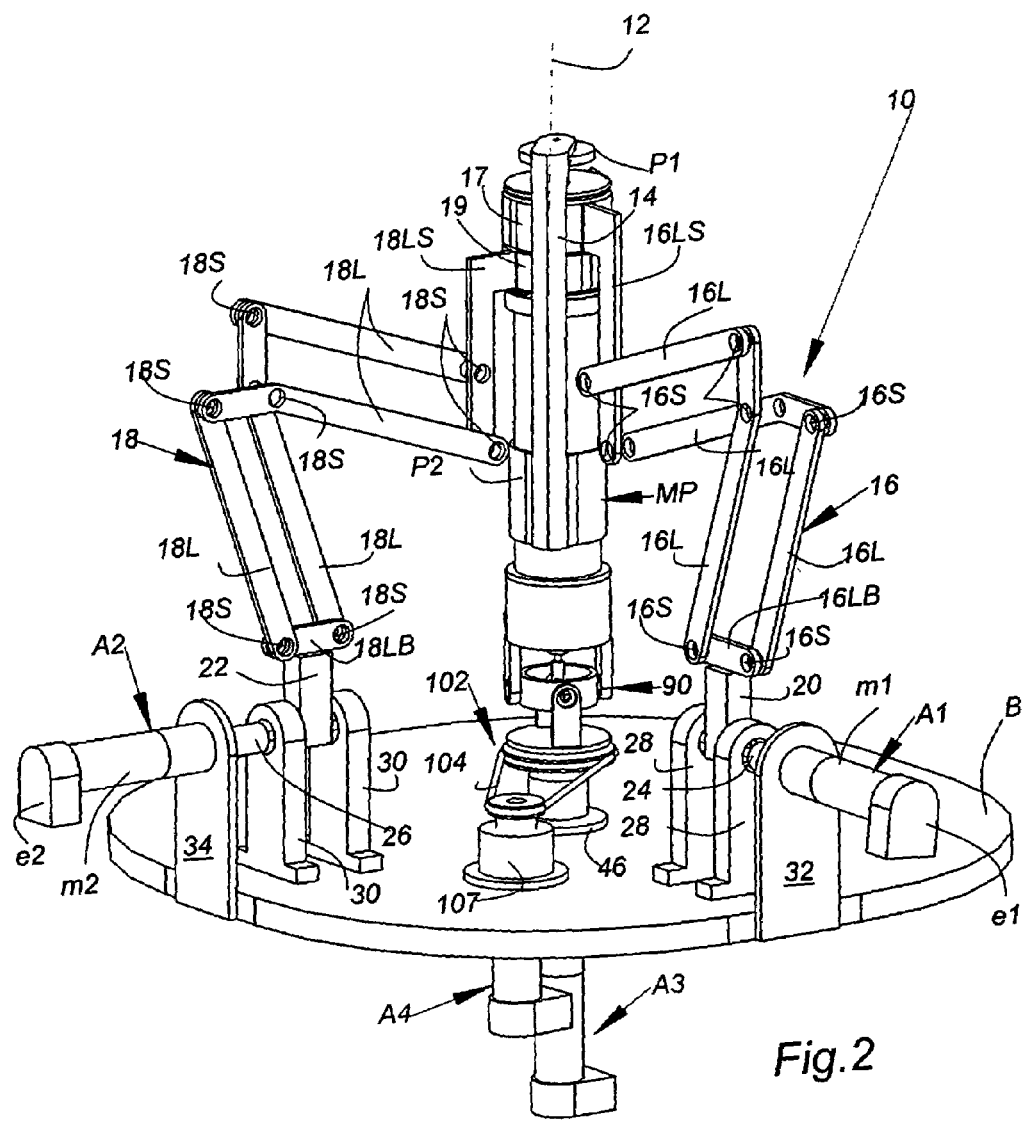
FIG. 2 is an isometric illustration of a preferred form of the present invention for use as a hand controller.
Figure 11:
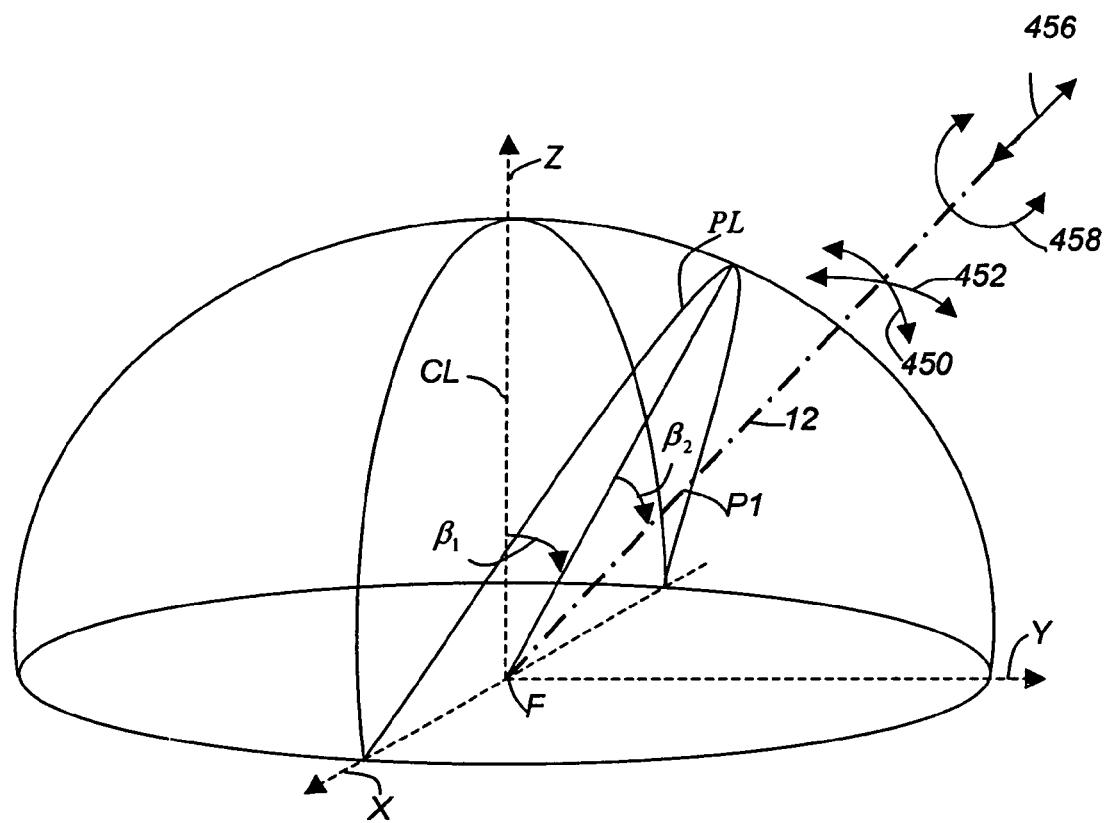
FIG. 11 is a schematic illustration of the movements of the end point.

The device 10 of FIG. 2 is preferably used as a controller or joystick and the device 10A of FIG. 11 is preferably used as a wrist.

The device 10 of FIG. 1 has moveable portion MP with a main axis 12 and is provided with an end point P1, which in the illustrated arrangement has a lever 14 rigidly connected thereto for movement relative to a base B (equivalent to table 4 of FIG. 1).

The first and second degrees of freedom (DoF) are each provided by identical mutually perpendicular six-bar pantograph 16 and 18, respectively, which permit the end point P1 (P2) to be manipulated in a hemispheric motion (or if used as a wrist when manipulated move the end point P1 to define a hemispherical motion) about a center point F (see FIG. 3), fixed relative to the base B and the location of which will be described below. The links 16L of the pantograph 16 are jointed together by shafts 16S and ball bearings (not illustrated) and the links 18L of the pantograph 18 are jointed together by shafts 18S and ball bearings (not illustrated).

The base link 16LB and 18LB of the pantographs 16 and 18, respectively are integral with their respective arms 20 and 22 which in turn are fixed to shafts 24 and 26 rotatably mounted on the base B on bearing pedestals 28 and 30, respectively.

The center point F is the intersection of the axes 24A and 26A of the shafts 24 and 26 (See FIG. 3) which are located in the same plane and as above indicated are mutually perpendicular to each other and the main axis 12. The length of the arms 20 and 22 are identical so that the offsets $a_1$ and $a_2$ of the links 16LB and 18LB, respectively from their respective shaft axis 24A and 26A are identical.

Each of the shafts 24 and 26 is provided with its respective actuator $A_1$ and $A_2$ which may take the form of a grounded electric motor $m_1$ and $m_2$, respectively, equipped with encoder $e_1$ and $e_2$, respectively, that determine the position or angular orientation of the shaft 24 or 26 relative to a base position. The actuators $A_1$ and $A_2$ are each fixed relative to the base B by mounting arms 32 and 34, respectively.

The sleeves 17 and 19 connect links 16LS and 18LS (links remote form the links 16LB and 18LB) of the pantographs 16 and 18 through suitable bearings as will be described below to the end point P1 so that movement of the pantographs 16 and 18 are transmitted to the end point P1 to move same about the center point F as described above. The links 16LS and 18LS provide essentially the same length offsets $a_3$ and $a_4$, respectively from the main axis 12 of the haptic 10.

The offsets $a_1$, $a_2$, $a_3$ and $a_4$ will normally all be of equal length and the lengths of the links between shafts will be set as in most conventional pantographs i.e. opposed links of equal length.

This assembly consisting of the two pantographs 16 and 18 provides for two degrees of freedom. Actuator $A_1$ turns and/or measures the turn of the pantograph 16 about the axis 24A (see FIG. 3) of the shaft 24 and thus turns (to apply force feedback to the operator when used as a Haptic or to manipulate the point P1 when used as a wrist) and/or measures one of the first two degrees of freedom and causes the links 18L to rotate on their respective shafts 18S. The other of the first two DoF is measured and/or controlled by actuator $A_2$ applies the same turning or measuring operations to pantograph 18 as the Actuator $A_1$ that applies to the pantograph 16 i.e. turns and/or measures the turn of the pantograph 18 about the axis 26A of the shaft 26 that causes links 16L to rotate about the their shafts 16S. It will be apparent that rotation of the pantographs 16 and/or 18 on their respective shafts 24 and 26 pivot the main axis 12 about the center point F (FIG. 3) so that the end point P1 is moveable to define a hemispherical motion about the center point F. It is also apparent that the first and second DoF are decoupled.

Figure 3:
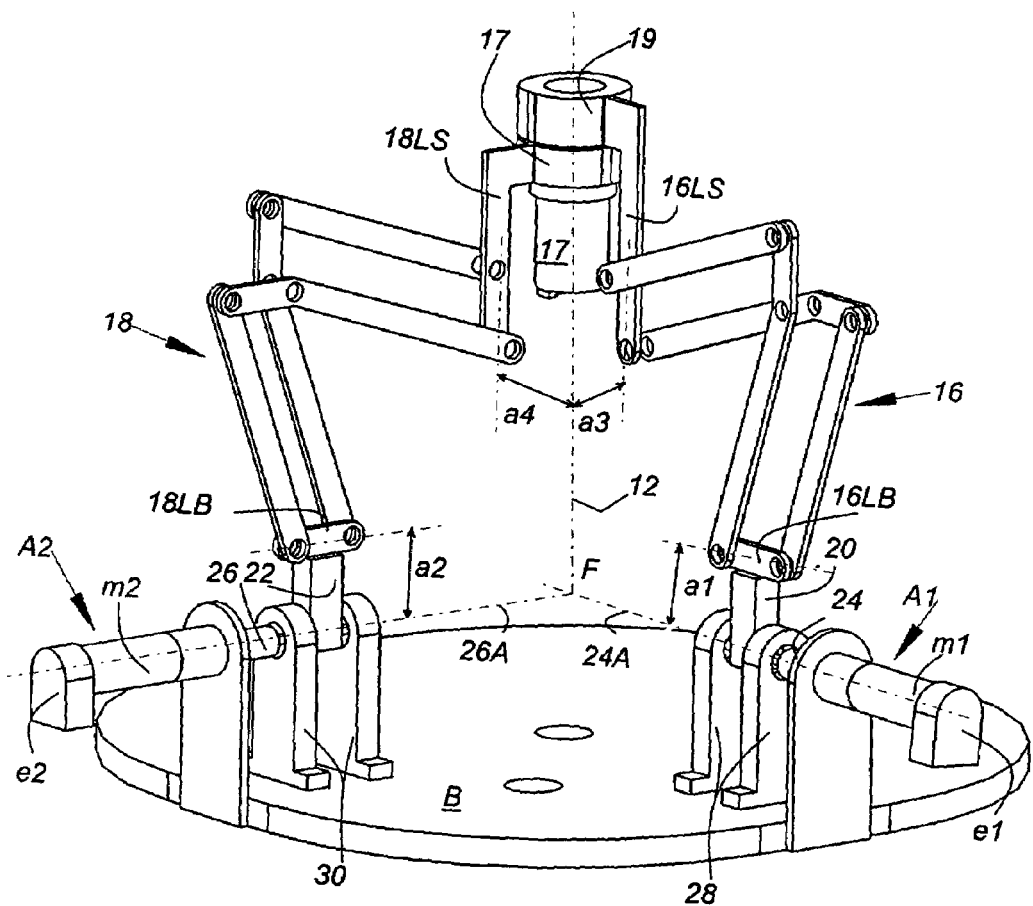
FIG. 3 is an isometric illustration with parts omitted showing the pantographs for applying the first and second Degree of Freedom (DoF) to the manipulated end point.

The third DoF provides a sliding motion along the main axis 12 which is also the radius of the hemisphere created by the first two degrees of freedom and which has its center at the center point F (see FIG. 3).

The operating system for this degree of freedom (see FIG. 4) includes an actuator $A_3$ that normally will include a direct drive electric motor $m_3$ and encoder $e_3$ that is connected to base B through flange (disk) 47. An inner universal joint 40 has one side 40a coupled to shaft 42 [which forms part of the first inner element that includes the system 50 (first portion) and slider 74 (second portion) to be described below] and its other side 40b (second side) coupled directly to the shaft 44 (second inner element) of the actuator $A_3$ and its pivotal axis 40c aligned with and defining the center point F. The shaft 44 is mounted for rotation relative to the base B by suitable ball bearings or the like schematically represented by the flange (disk) 46 in FIG. 4. Shaft 44 can be connected to the shaft of the actuator $A_3$ preferably by a suitable coupling such as the one shown in as part 45 in FIG. 9.

A belt or cable drive system 50 (first portion) (see FIGS. 4 and 5) drives or is driven by the pulley 52 fixed to shaft 42 and incorporates a plurality of guide pulleys 54 and a turn around pulley 56 that are arranged to insure the closed-loop cable 58 travels in a path having a significant portion of its travel substantially parallel to the axis 12.

Figure 5:
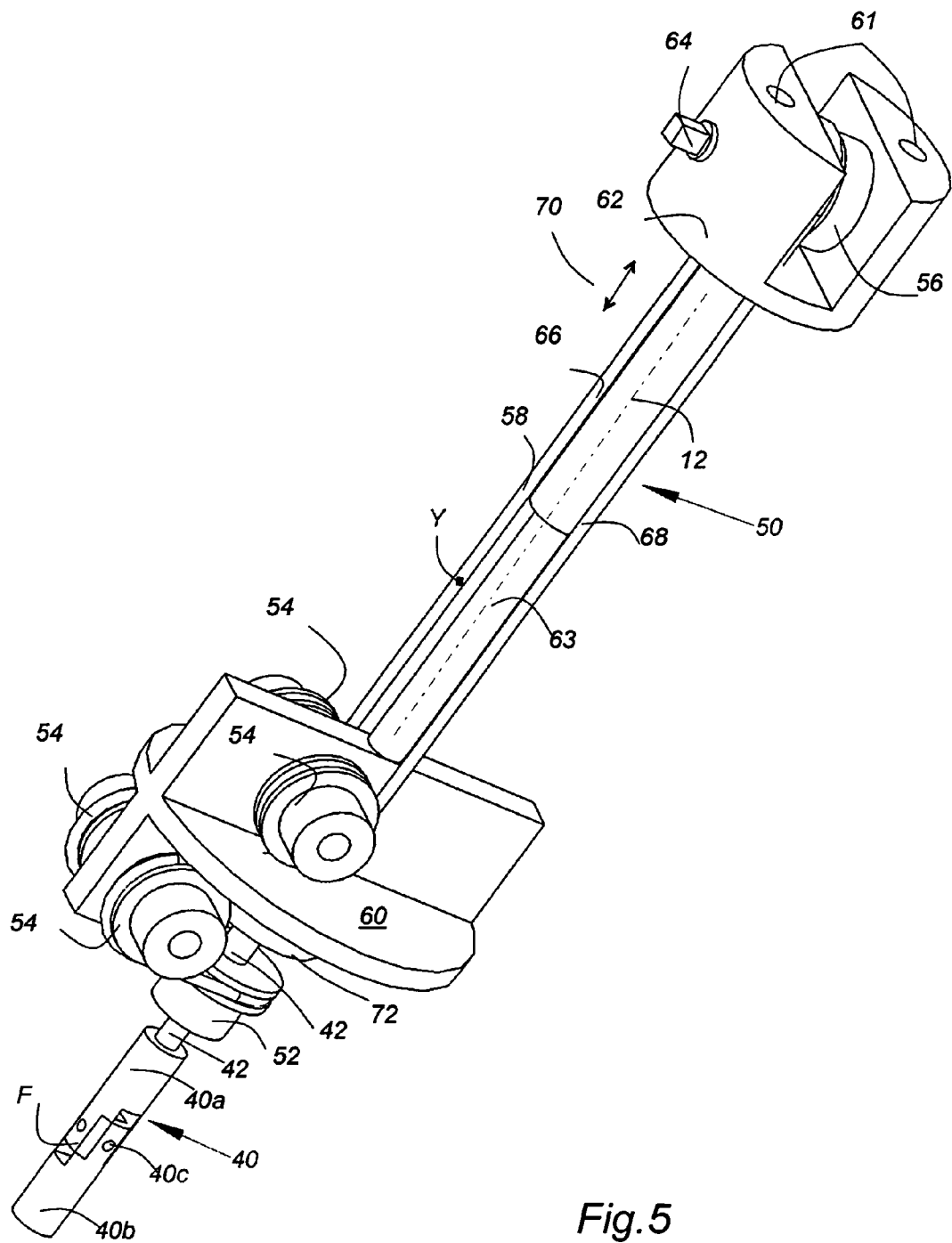
FIG. 5 is an isometric illustration with parts omitted showing in greater detail the belt drive system for applying the third DoF to the manipulated end point shown in FIG. 4.

As shown in FIG. 5 pulleys 54 are mounted on a first normally lower support 60 on which a second normally an upper support 62 for mounting the pulley 56 is preferably adjustably mounted via a connection schematically represented by the shaft 63 from the lower support 60. The upper support 62 mounts the turn around pulley 56 to form the cable or belt runs 66 and 68 that are substantially parallel to and are moved by rotation of the pulley 52, 54 and 56 in a direction substantially parallel to the axis 12 as indicted by the arrow 70.

Figure 6:
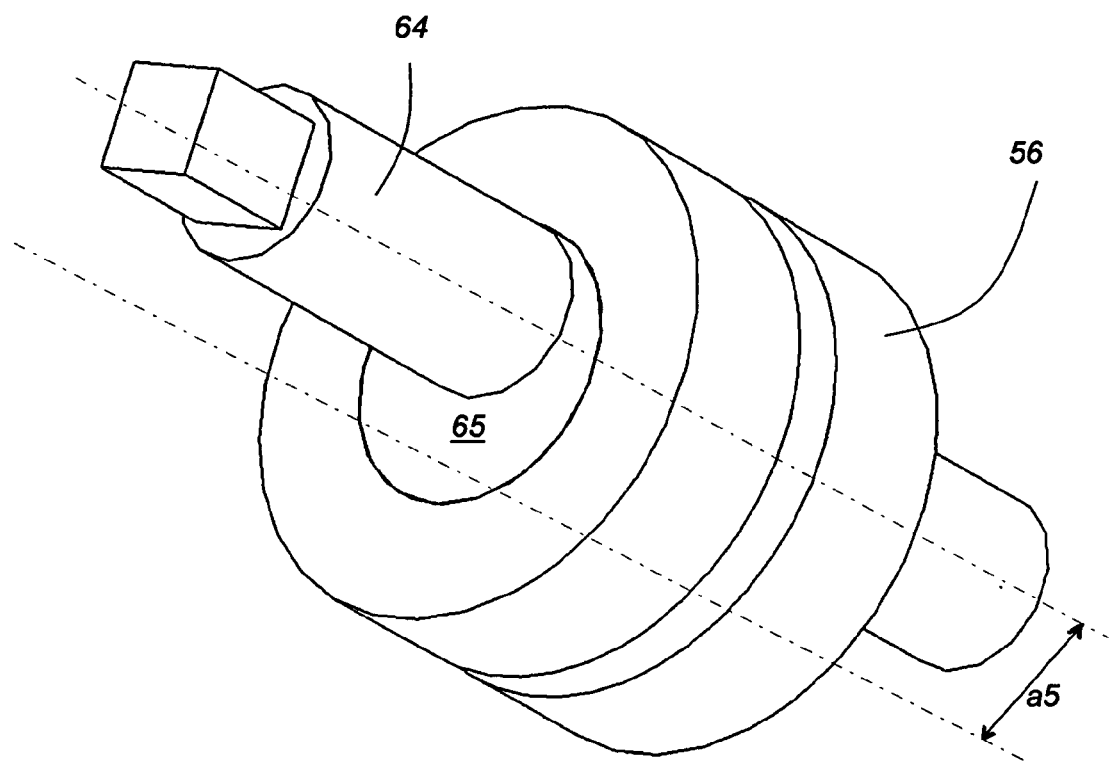
FIG. 6 is an isometric illustration of one form of adjustment mechanism for adjusting the tension in the belt drive for the third degree of freedom.

As shown in FIG. 6 the tension in the belt or cable 58 is adjusted by turning the shaft 64 which has an offset portion 65 on which the pulley 56 rotates and which provides an offset $a_5$ so that rotation of shaft 64 changes the position of the periphery of the pulley 56 relative to pulley 54 to thereby adjust the tension in the belt or cable 58. The shaft 64 is locked into adjusted position by any suitable means in the illustrated arrangement. A setscrew, for example, may be provided in the lower portion of the holes 61 (see FIG. 5) to engage and lock the shaft 64 on opposite sides of the pulley 56.

The lower support 60 is mounted via a suitable decoupling bearing structure 72 on the axial end of shaft 42 remote from the universal joint 40 so that the shaft 42 rotates freely relative to the support 60.

Figure 7:
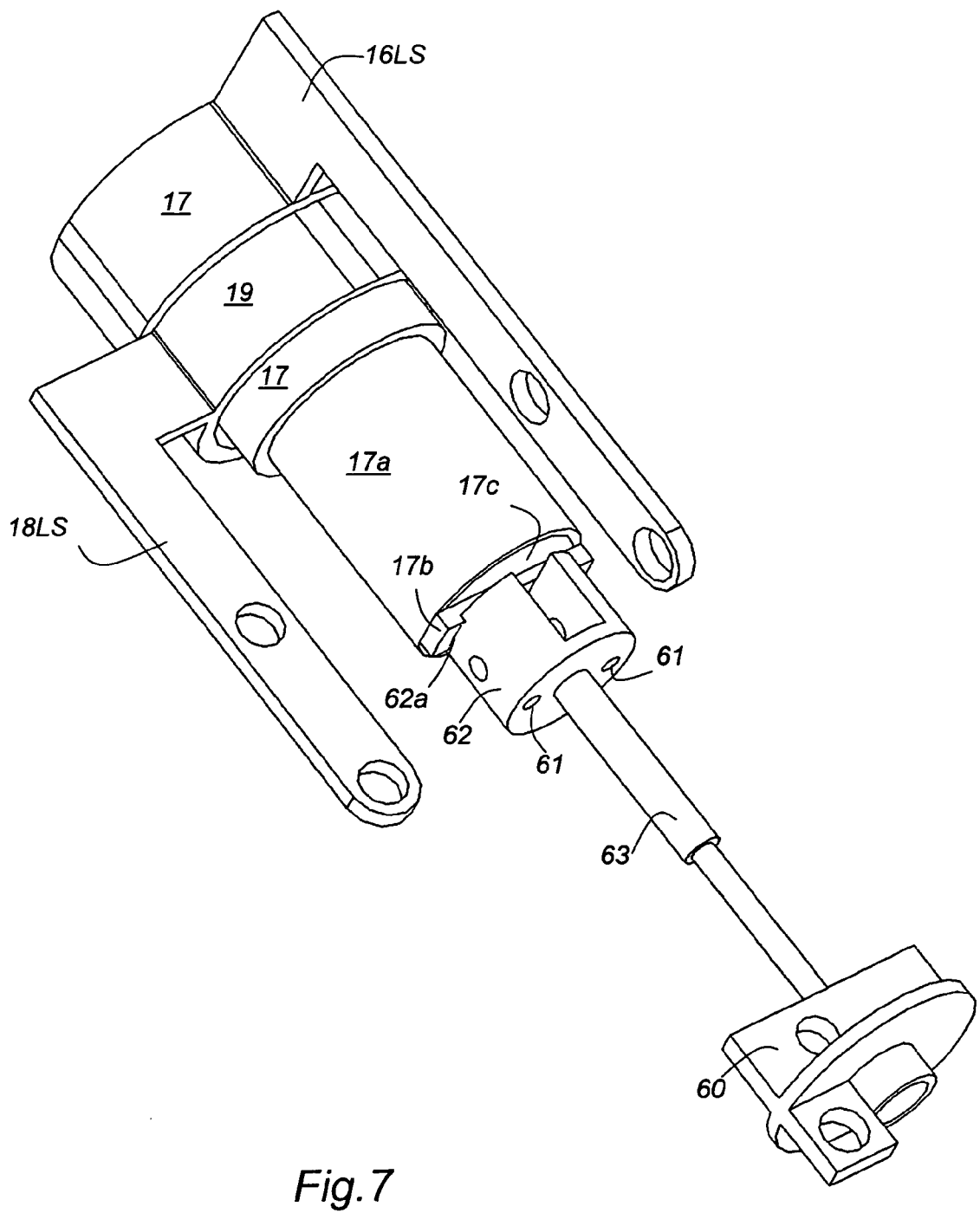
FIG. 7 illustrates the interconnection of the pulley mounting for the third degree of freedom with the sleeve connected to one of the pantographs of the first and second degrees of freedom.

The support platform 60 and the rest of the cable drive system 50 may be prevented from rotation by any suitable means a preferred form of which is illustrated in FIG. 7. In the illustrated arrangement the support 62 is coupled to a lower portion 17a of the sleeve 17 by a tongue formed by a cross bar 17b on the sleeve 17 and a mating groove 62a provided on the support 62. Also bolts (not shown) pass through holes (not shown) in the bar forming tongue 17b are threaded into the upper portions of the threaded holes 61 to firmly secure support 62 and sleeve 17 together. The bar 17b provides extend diagonally across the sleeve which is hollow and provides spaces 17c one on each side of the bar 17b (only one shown) that permits the struts 74a and 74b to be received therein so that the top end member 74c is moved up and down within the sleeve 17 as will be described below.

The slider 74 is made of several parts namely a pair of opposed struts 74a and 74b connected at their opposite ends by end members 74c and 74d. When the device is assembled, the bar 17b slides across the slider 74 between the struts 74a and 74b on the side of the top end member 74c remote from the shaft 76 and then connected to the sleeve 17 as shown.

Figure 4:
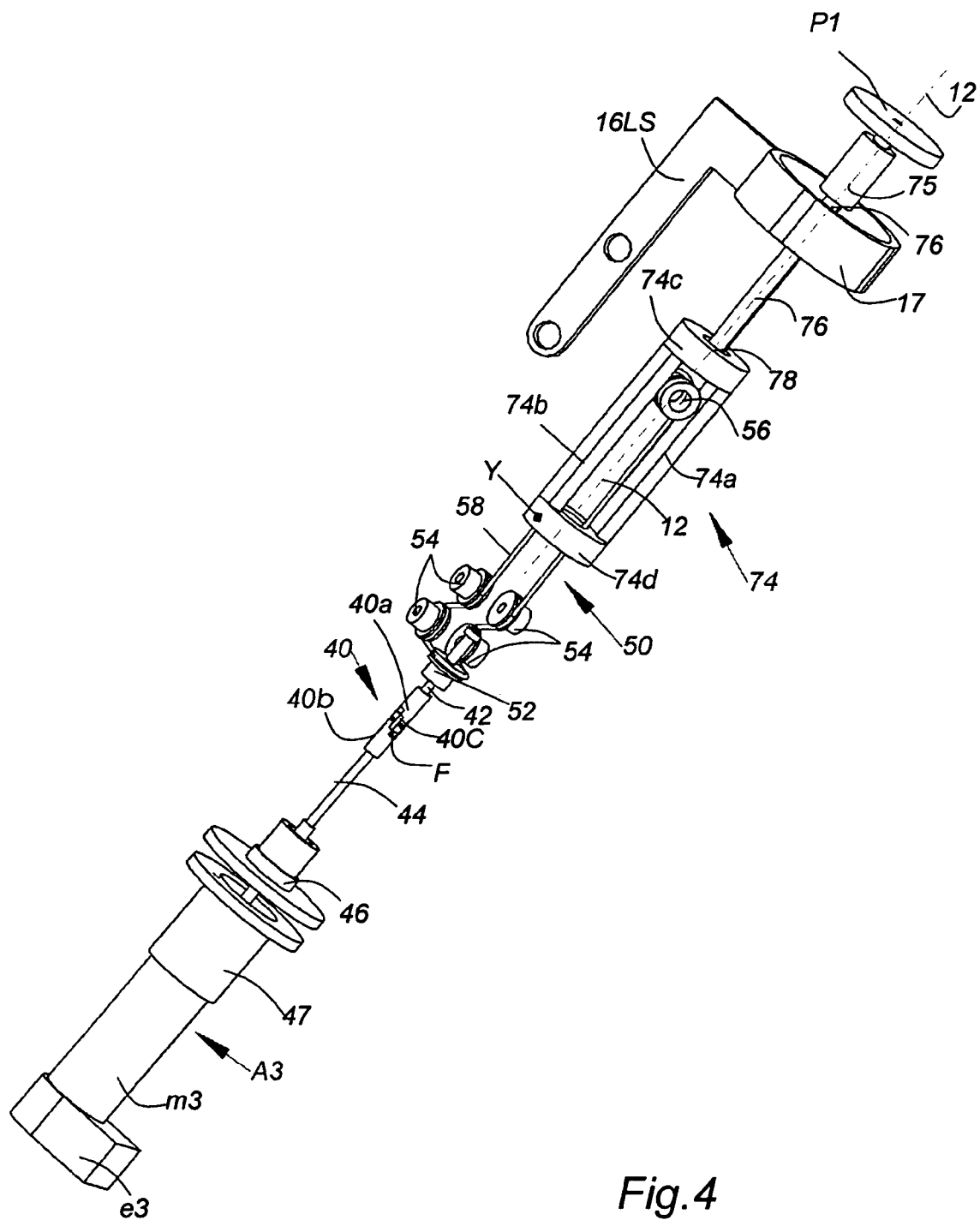
FIG. 4 is an isometric illustration with parts omitted showing one preferred arrangement for applying the third DoF to the manipulated end point.

A slider 74 (second portion) is fixed to one side of the cable route 58 at point indicated as point Y (FIG. 4) and is connected to a ball spline and shaft 76 system through a ball bearing 78 (FIG. 4). The ball bearing 78 decouples the rotational motion of the ball spline shaft 76 from the slider 74. The ball spline shaft 76 as is well known is a linear motion system, in that balls accommodated in the spline nut 75 transmit torque while permitting linear or axial movement on precision raceways on a spline shaft.

The other side of the cable 58 passes through slider 74 without any contact with the slider 74.

The cable drive system 50 particularly the cable 58 converts the rotational motion of the actuator $A_3$ and the inner universal joint 40 into the sliding one of the slider 74.

The axis of the sliding motion of the slider 74 is concentric with the main axis 12 of the device (FIGS. 2, 3 and 4). The universal joint 40 allows the third degree of freedom to idly follow the first two DoF provided by the pantographs 16 and 18 while transmitting rotational motion of its own degree of freedom.

The end point P1 is in the illustrated arrangement is at the end of shaft 76 remote from the base B and may be connected directly to other elements such as handle 14 to achieve the desired purpose.

Figure 8:
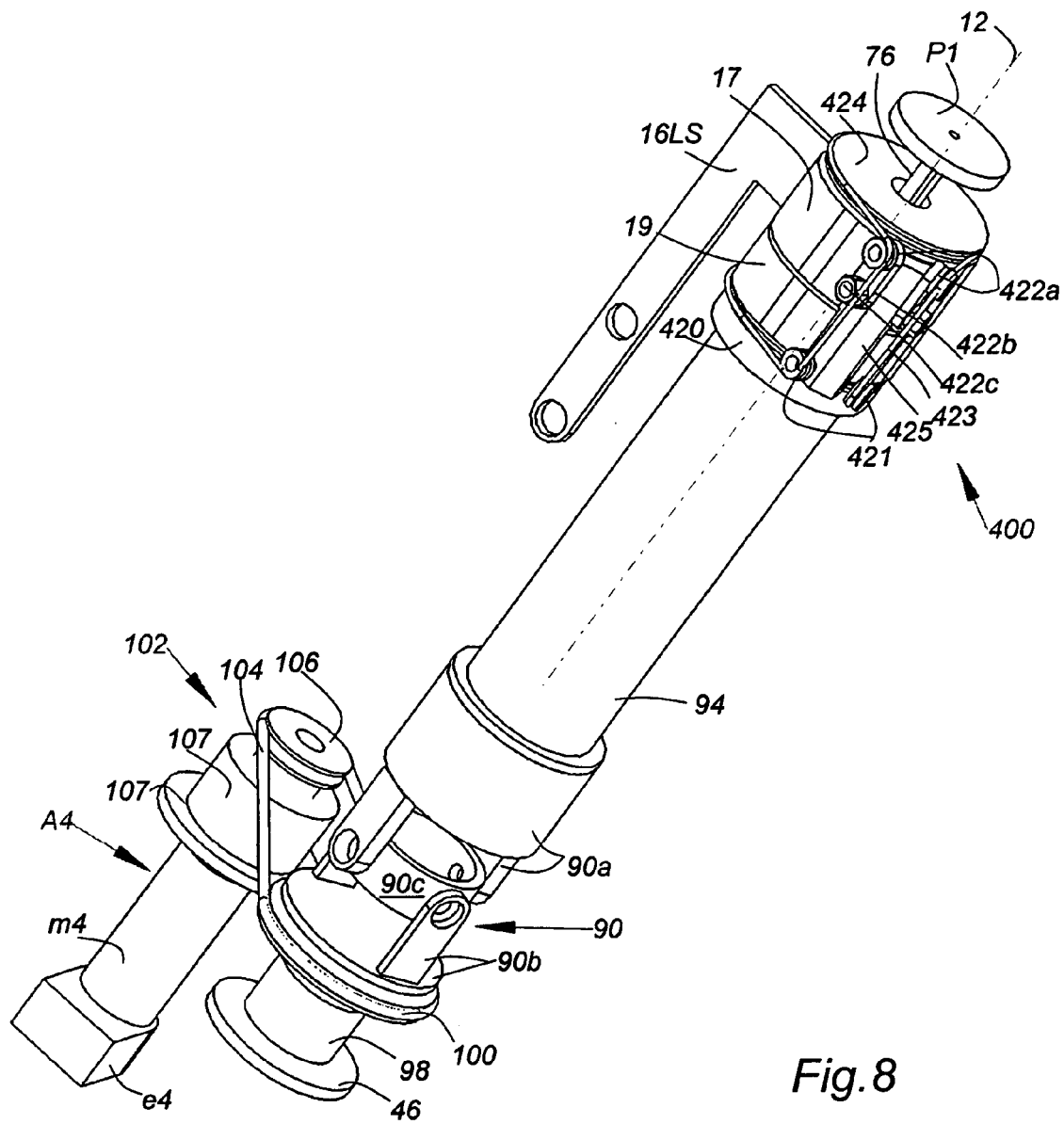
FIG. 8 is an isometric illustration with parts omitted showing a preferred arrangement for delivering rotational movement to the end point i.e. for applying the fourth DoF to the manipulated end point.
Figure 9:
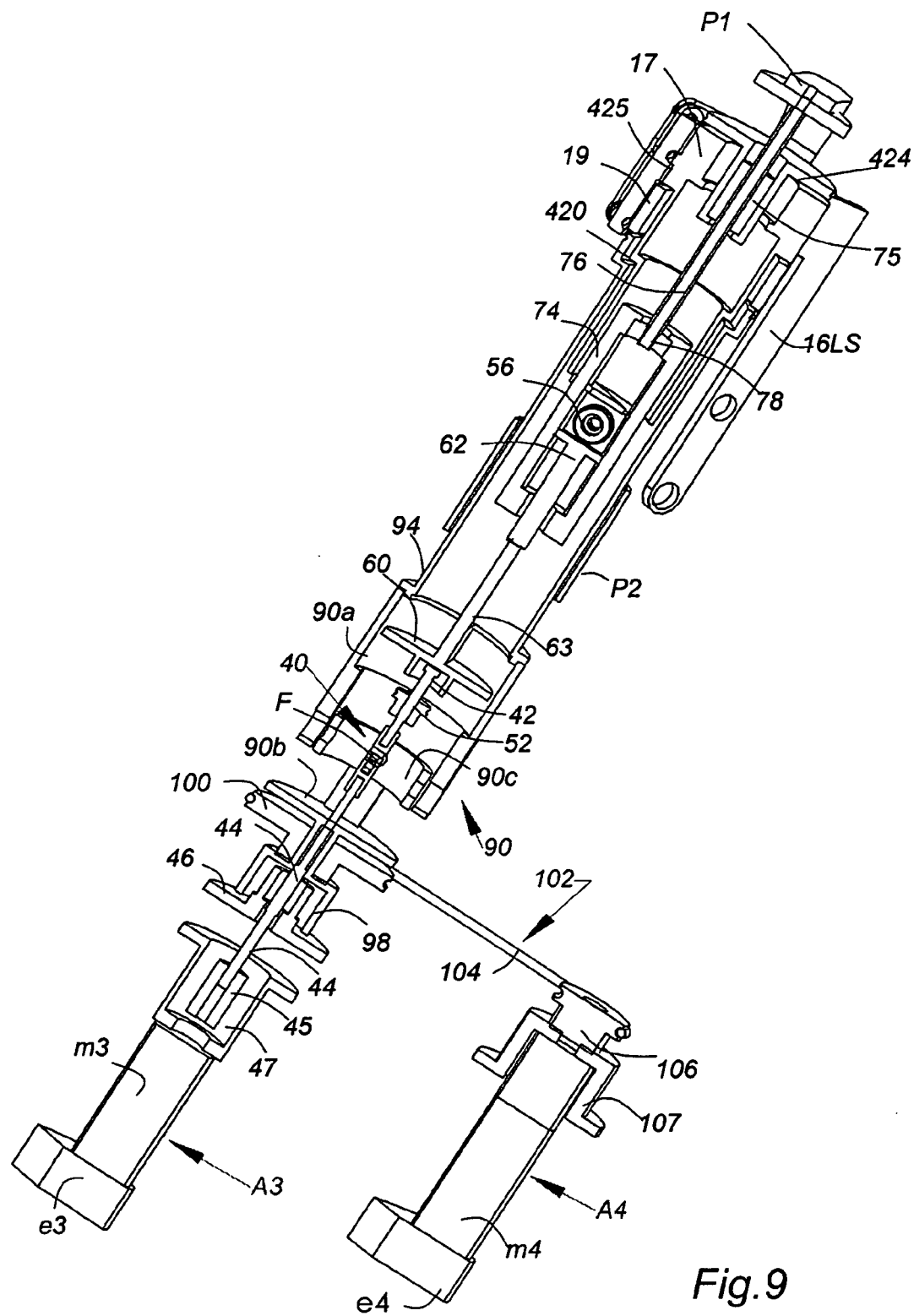
FIG. 9 is an isometric cross-section illustration with parts omitted showing inter-relationship of the elements for applying the third and fourth DoF to the end point.

The fourth subassembly illustrated in FIGS. 2, 8 and 9 is optional and is only provided if the system is to have 4 DoF i.e. if rotational motion of the end point P1 is to be provided. The axis of rotation is concentric with the main axis 12, which is concentric with the shaft 76 and 42 and with the sleeves 17 and 19.

Referring to FIG. 8 this fourth DoF is provided by an outside universal joint 90 concentric with the inner universal joint 40 (see FIG. 9) so its pivot point is also aligned with the center point F. One or a first side 90a of the outer universal joint 90 is connected to a first outside element 94 that as will be described below is connected to the shaft 76 to apply rotational forces thereto and thereby to the end point P1. A second side 90b of the outside universal joint 90 is mounted on the base B via a suitable rotatable pedestal 98 that rotates on the base B via bearings mounted on flange (disk) 46. A pulley 100 of the belt or cable drive system 102 is fixed to rotate with the pedestal 98 to drive or be driven by the universal 90 as will be described below. The outer universal 90 has a hollow ring 90c to which the sides 90a and 90b are pivotably connected in the conventional manner to provide that hollow interior in which the inner universal 40 is received.

The belt or cable drive system 102 further includes a belt or cable 104 that drivingly connects the pulley 100 to the pulley 106 of the Actuator $A_4$. The actuator $A_4$ will normally include a grounded electric motor $m_4$ and encoder $e_4$, to drive and/or monitor the movement of the element 94. The actuator is fixed to the base B through flange 107. A preferred form of drive for fourth degree of freedom is illustrated in FIGS. 8 and 9 and represents rotation on an axis of rotation concentric with the main axis 12.

The power train for this subassembly consists of belt or cable drive system 102 described above and the second cable drive 400. The second cable drive 400 consists of an lower pulley 420 embedded in the upper part of connecting tube 94, two guiding pulleys 421, two tension adjuster mechanisms 422, closed loop cable 423 and an upper pulley 424 which is connected to and drives the spline nut 75 about the axis 12. The upper pulley is mounted on the sleeve 17 via ball bearings (not shown) that permit the pulley 424 is, mounted on the sleeve 17 via decoupling ball bearings (not shown) that permit the pulley 424 to freely rotate on the axis 12 relative to the sleeve 17. The guiding 421 and the tension adjuster pulley 422 are mounted on sleeve 17 of link 16LS block by block 425. The tension adjuster mechanism consists of pulleys 422a, links 422b and tightening nuts 422c. By turning and tightening the link 422b and the nut 422c, respectively, the user is able to adjust the cable tension. Cable 423 transmits motion from lower pulley 420 to upper one 424. The ball spline nut 75 permits relative axially movement between the pulley 424 and the shaft 76 while transmitting rotational movement there between. The ball spline nut 75 is fixed to upper pulley 424.

The connecting tube or housing 94 is jointed to sleeve 17 of link 16LS of the pantograph 16 through a ball bearing (not shown) that decouples the rotational motion of connecting tube 94 from link 16LS.

Figure 10:
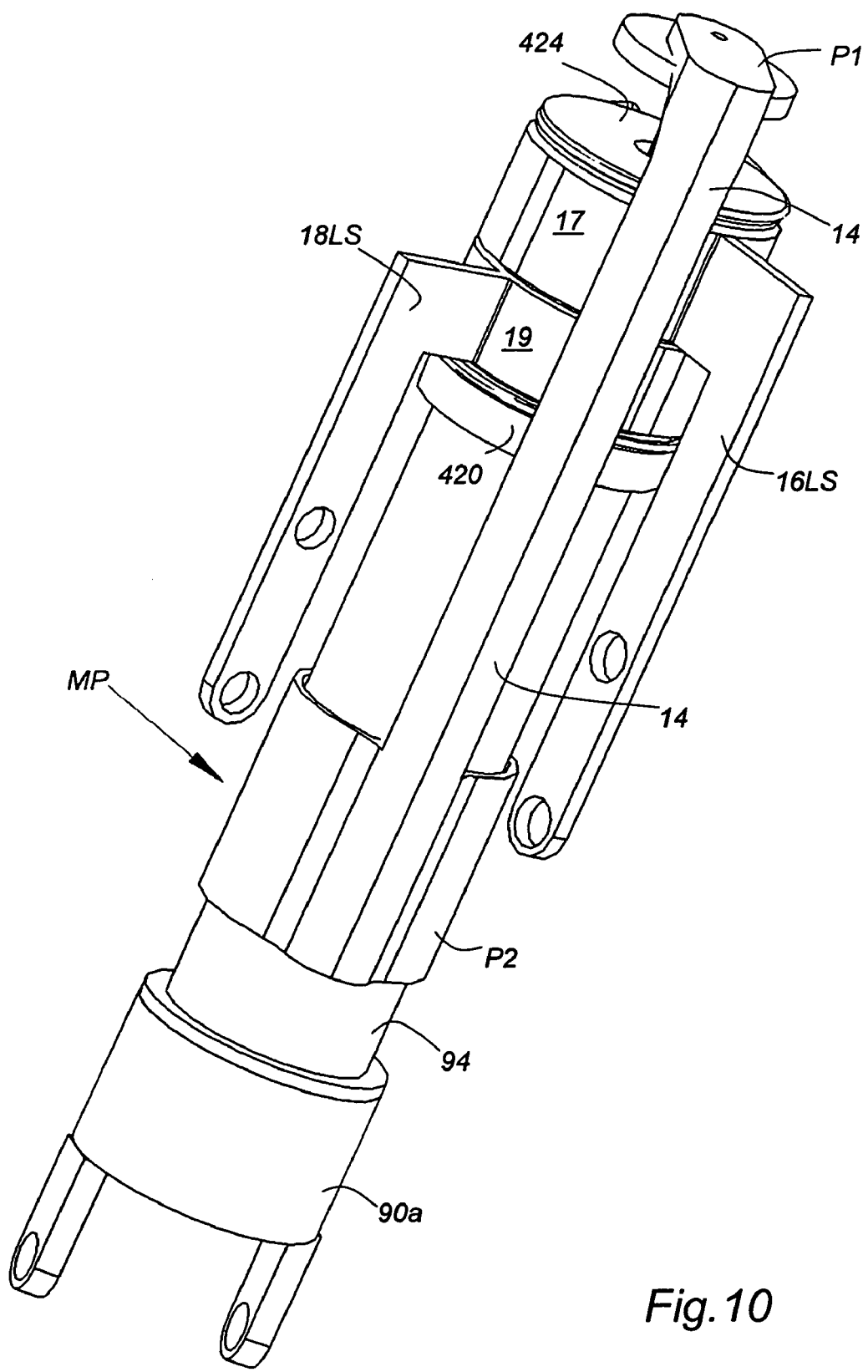
FIG. 10 is an isometric illustration with parts omitted showing in greater detail the connection between the pantographs for the first and second DoF to the manipulated end point.

In some cases it may be desirable to have a sleeve P2 or the like that encircles the controller 10 and is connected to the handle 14 to provided an auxiliary end point P2 which may be grasped by the user by either one of or both hands to facilitate manipulation of the haptic 10. This construction allows the user to hold the handle in two places i.e. one hand on top at P1 and another encircling the housing 94 at P2. In order to maneuver the housing 94 at P1, the operator must mainly move her/his elbow and upper arm. Maneuvering the housing 94 at P2, on the other hand, requires the movement of the hand about the wrist only. Such an arrangement is shown in FIG. 10.

In the illustrated version the handle 14 has been shown located in the 90° segment between the pantographs 16 and 18 for convenience so it is visible, it will normally be on the opposite side i.e. in the 270° segment between the pantographs 16 and 18 to provide 270° of free movement. It will be apparent that if 360° movement is desired the handle 14 may be eliminated.

Turning to FIG. 11 wherein the operation of the device is illustrated schematically the centerline CL indicates the datum centerline of the device and assuming the device is oriented vertically this line CL will extend vertically from the center point F. The axis 12 is manipulated so that the plane PL containing the point P1 extends at any suitable selected angle $\beta_1$ measured from the CL about X axis (assuming CL is the Z axis) and the point P1 is at second selected angle $\beta_2$ measured from the Z axis of CL on plane PL about the Y axis. These angles $\beta_1$ and $\beta_2$ are determined by the pantographs that have been pivoted from their respective datum positions which for the purpose of this description is the location when the centerlines CL and 12 coincide. In effect rotation of the pantographs 16 and 17 on their respective axes 24A and 26A result in mutually perpendicular displacements of the centerline 12 relative to centerline CL as indicated by the arrows 450 and 452. Thus, movement of the pantographs 16 and 18 about their respective axes 24A and 26A results in adjusting the size of angle $\beta_1$ and $\beta_2$ and thereby the positioning of point P1 relative to the centerline or axis CL.

The third degree of freedom moves the end point P1 axially along the axis 12 as indicated by the arrow 456 in FIG. 11 and the fourth degree of freedom rotates the end point P1 around the axis 12 as indicated by the arrow 458.

The above-described combination preferably will be used as a haptic controller i.e. a joystick with force reflecting capability. It may be used to control the motion of, and reflect the forces from a remote wrist performing selected operations such as palpation or ultrasound diagnosis.

Preferred Form of Wrist

Similar parts of the controller 10 described above to those equivalent parts of the wrist 10A are called by similar names in the following description of the wrist 10A which as above indicated may also be used as a controller or haptic.

Figure 12:
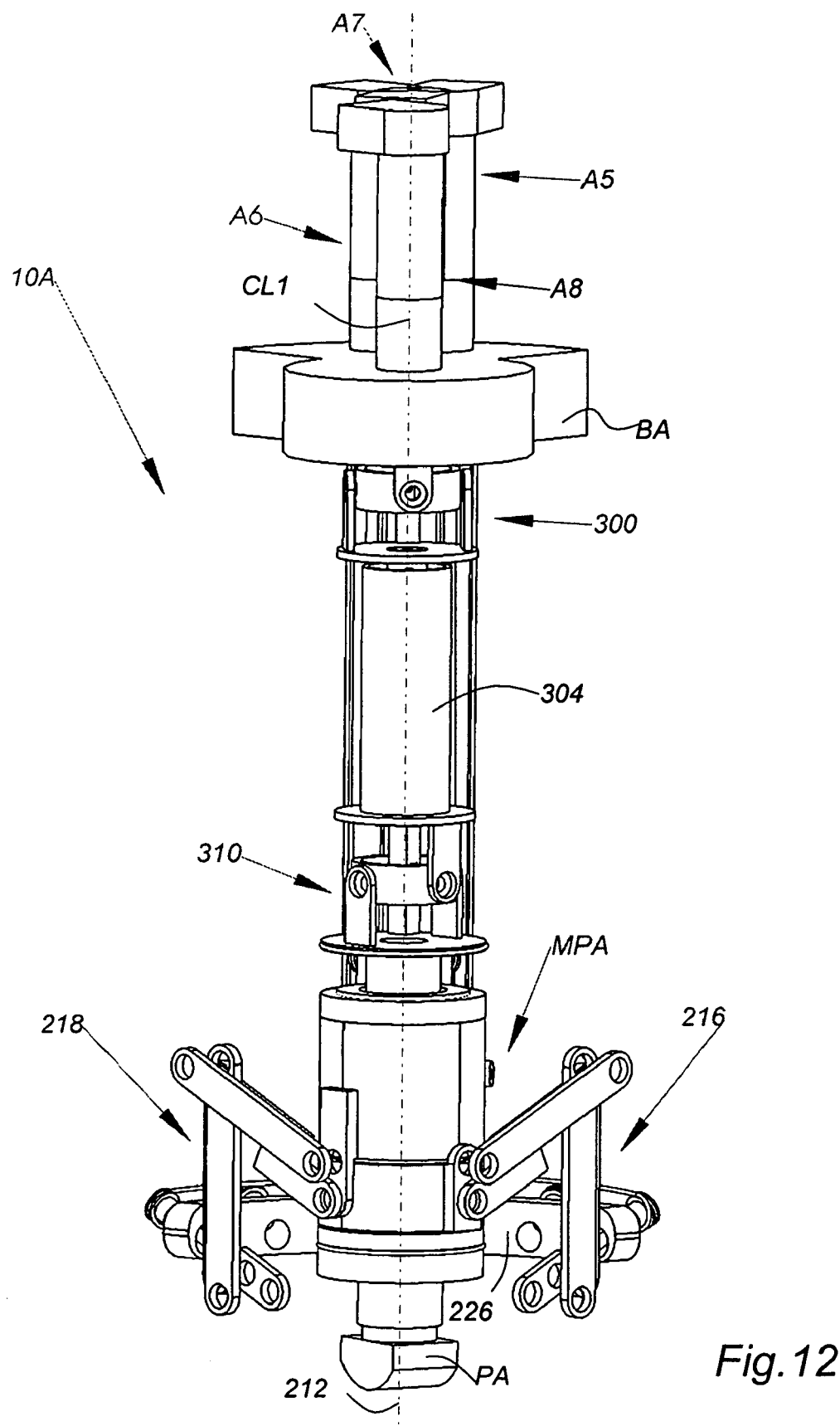
FIG. 12 is a general isometric illustration with some parts omitted showing the wrist structure of the present invention.
Figure 13:
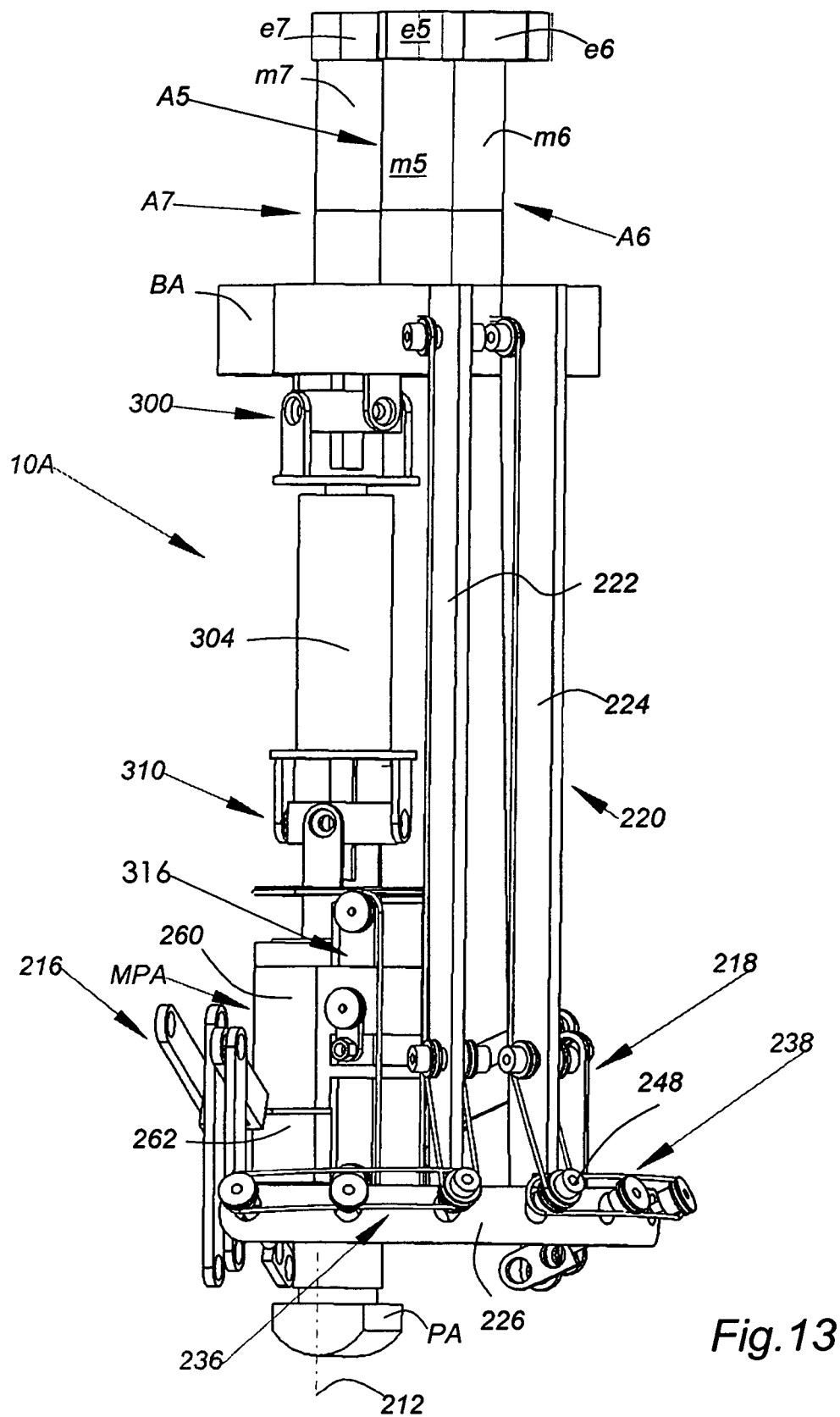
FIG. 13 is a general side elevation view of a preferred form of the device of the present invention for use as a wrist.

Referring to FIG. 12, the device 10A which may function as either a haptic or controller or a wrist and which preferably is used as a wrist in the present invention is provided with moveable portion or section MPA having a main centerline 212 and end point or probe PA that is being manipulated. This probe PA is primarily manipulated about a center point or a center-of-motion point FCM (see FIG. 14). The probe PA may also be manipulated as will be described below for axial and or rotational motion relative to the main centerline 212 of the main or moveable section MPA in which the operating modules (described below) are to be amounted. This moveable section MPA is oriented as will be described below by a pair of pantographs 216 and 218 which operate or are operated to orient the section MPA particularly the probe PA in a manner similar to the operation of the pantographs 16 and 18 in the positioning of the end point P1.

A pair of six-bar pantographs 216 and 218 similar to the pantographs 16 and 18 of the above-described controller are mounted on a frame 220 suspended from the base BA defines the first two DoF of the probe PA (which is the wrists equivalent to the end point P1 and is manipulated in a manner similar or equivalent to the movements of the end point P1 of the haptic or controller 10 described above). The frame in the illustrated arrangement (see FIGS. 13 and 17) is formed by a pair of pillars 222 and 224 to which is attached a substantially semi circular bar 226 on which the turning axels 228 and 230 (see FIG. 14) of the pantographs 216 and 218 are mounted.

The axes 232 and 234 of the axles 228 and 230 are positioned in their corresponding axial planes 90 degrees apart. These axes 232 and 234 are set at the same selected angel a relative to the main axis 212 so that they are in effect in the same cone relative to the datum centerline CL1 of the moveable section MPA which is equivalent to the centerline CL of the device 10 described above and is thus coaxial with the axis 212 when the axis 212 is in neutral position—in the illustrated arrangement when the axis 12 is substantially vertical.

The point of intersection of projections of axes 232 and 234 with each other and with main axis 212 (and with the centerline CL1) defines the location of the center-of-motion point FCM.

Figure 14:
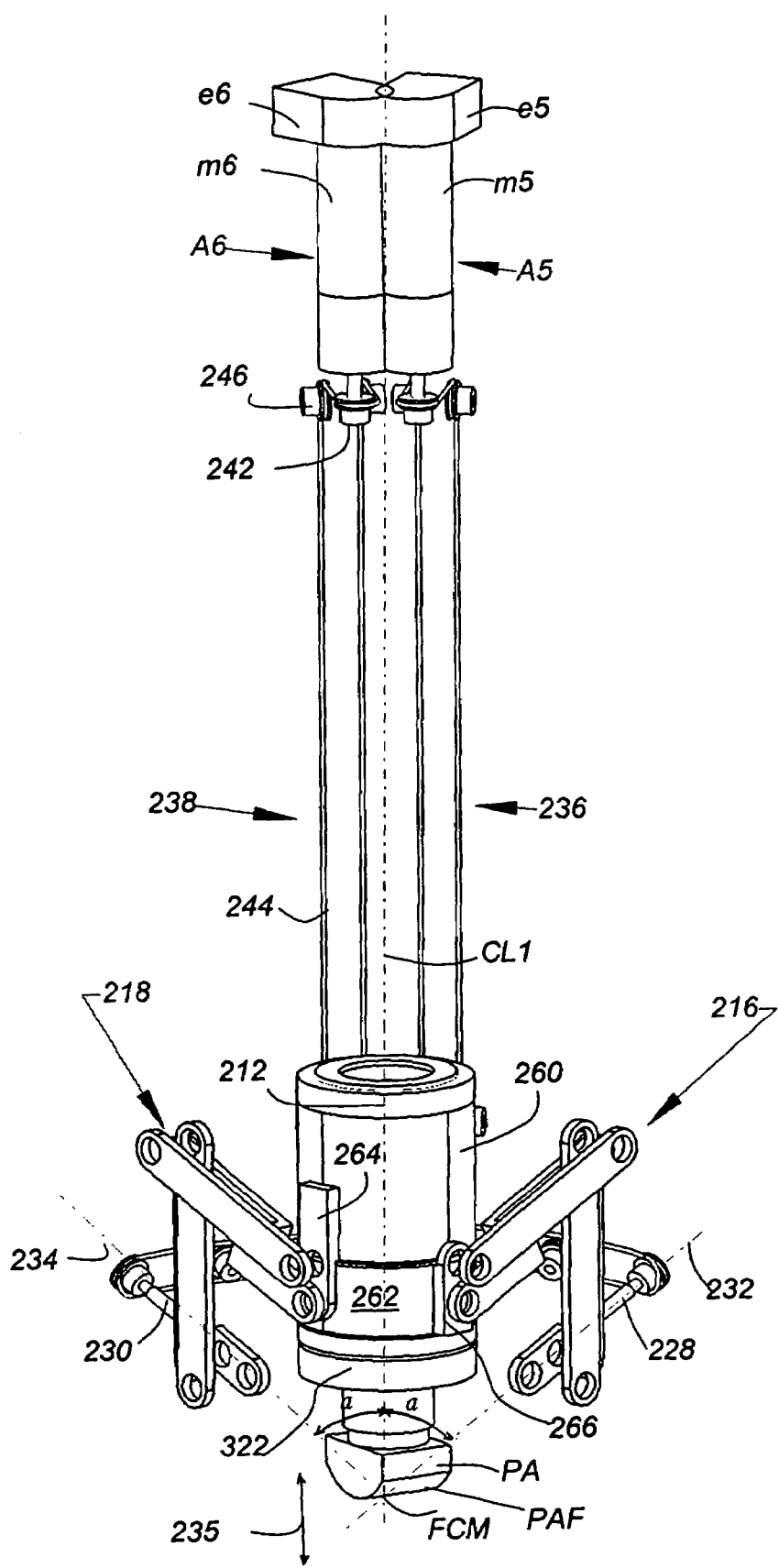
FIG. 14 is an isometric illustration with parts omitted showing the location of the center-of-motion of the device.
Figure 15:
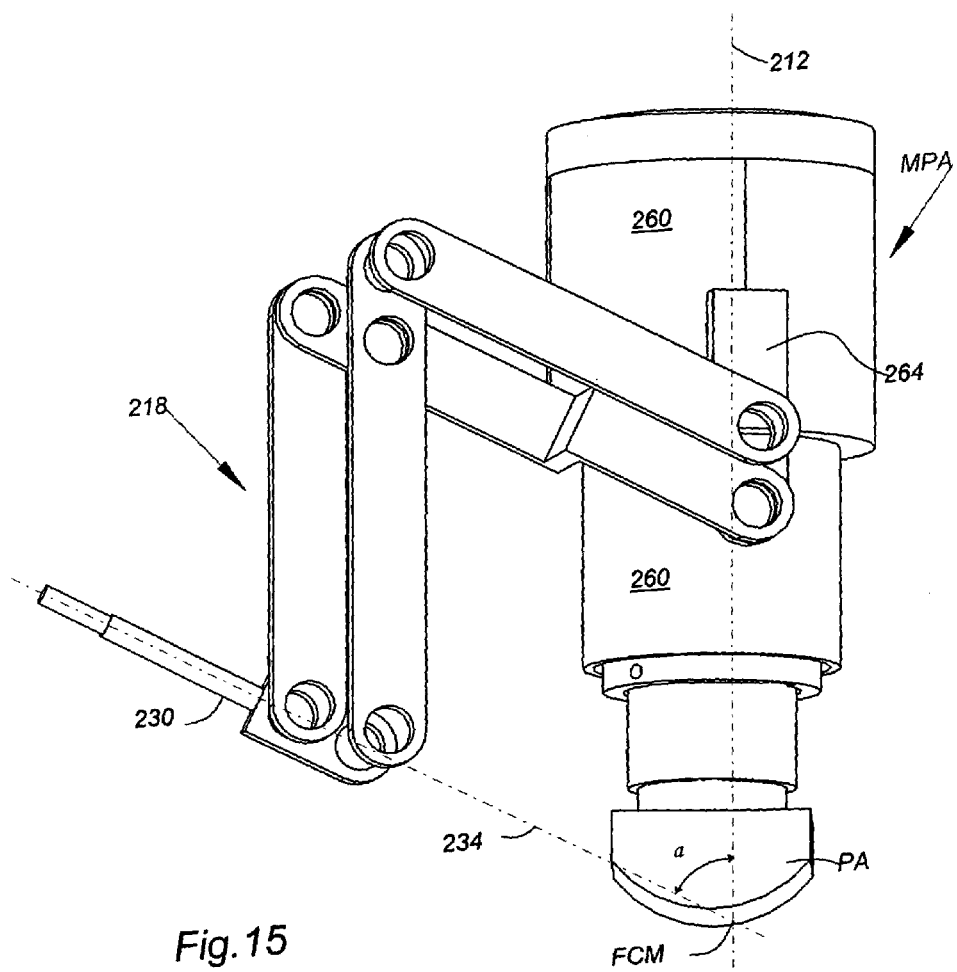
FIG. 15 is an isometric illustration with parts omitted showing in greater detail one of the pantographs for applying the first or second DoF movements of the end point.
Figure 16:
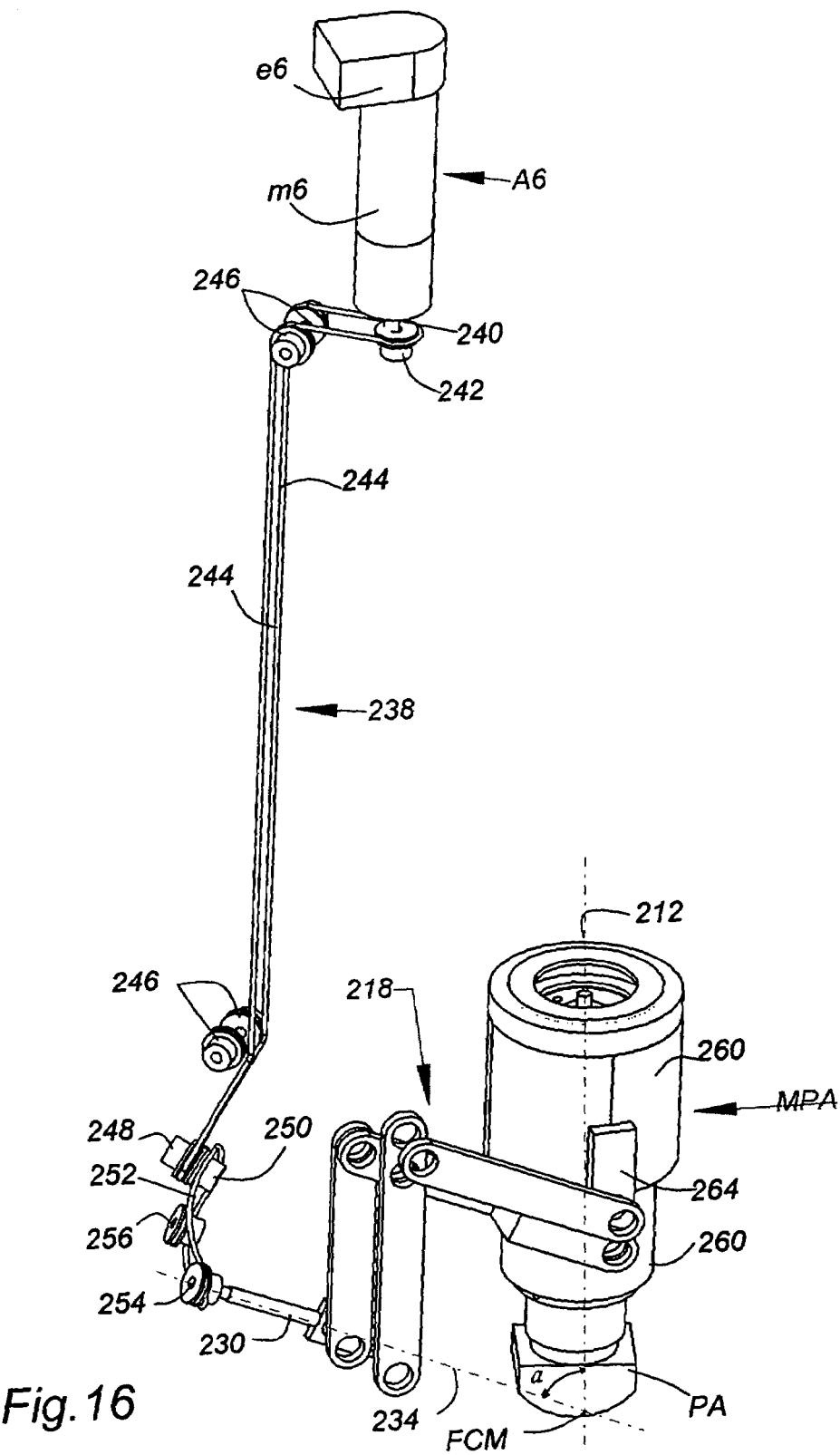
FIG. 16 is an isometric illustration with parts omitted showing the belt drive arrangement for applying the driving forces to or from the pantograph(s) for controlling the first and second degrees of freedom DoF of the preferred form of wrist device.
Figure 17:
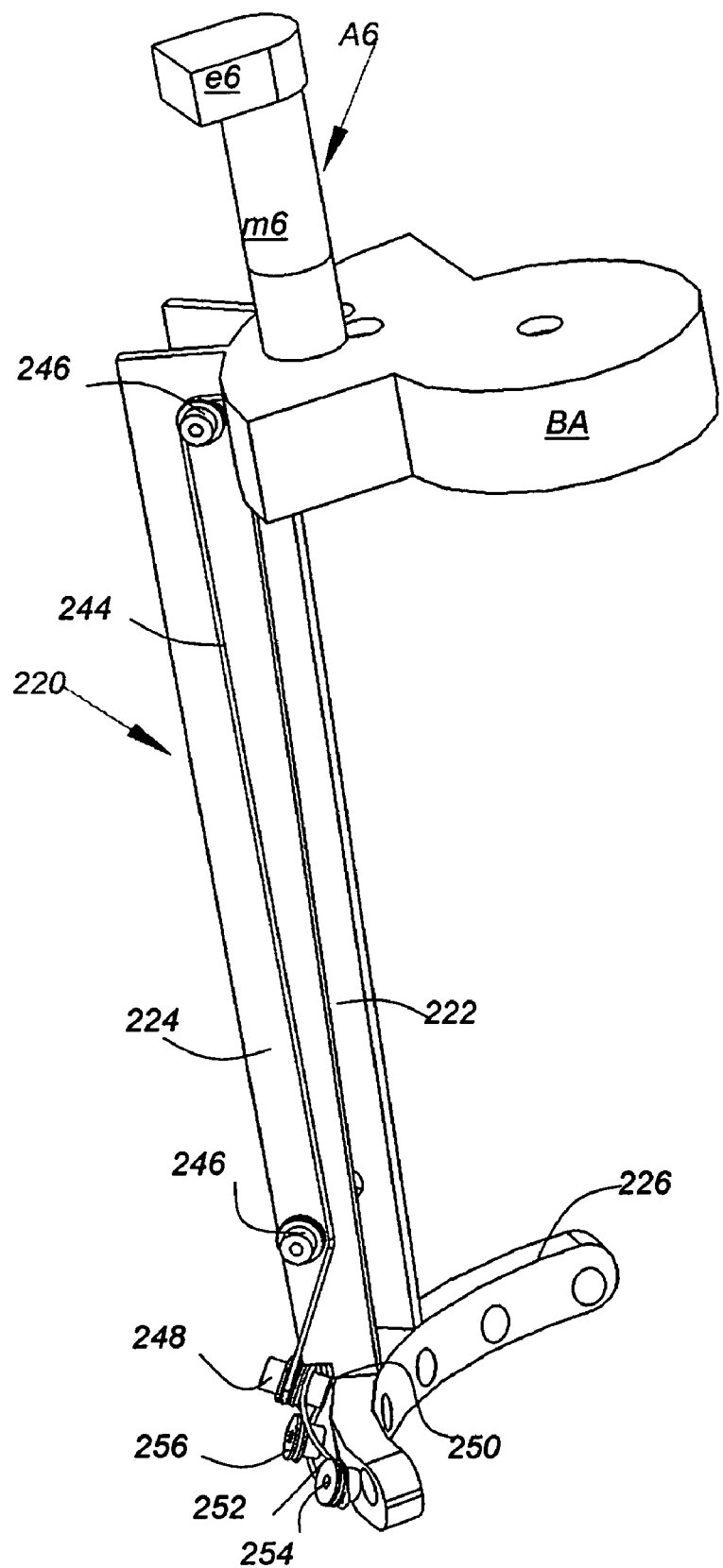
FIG. 17 is an isometric illustration with parts omitted showing the support arrangement for the cable drive arrangement pantographs for the preferred form of wrist device.
Figure 18:
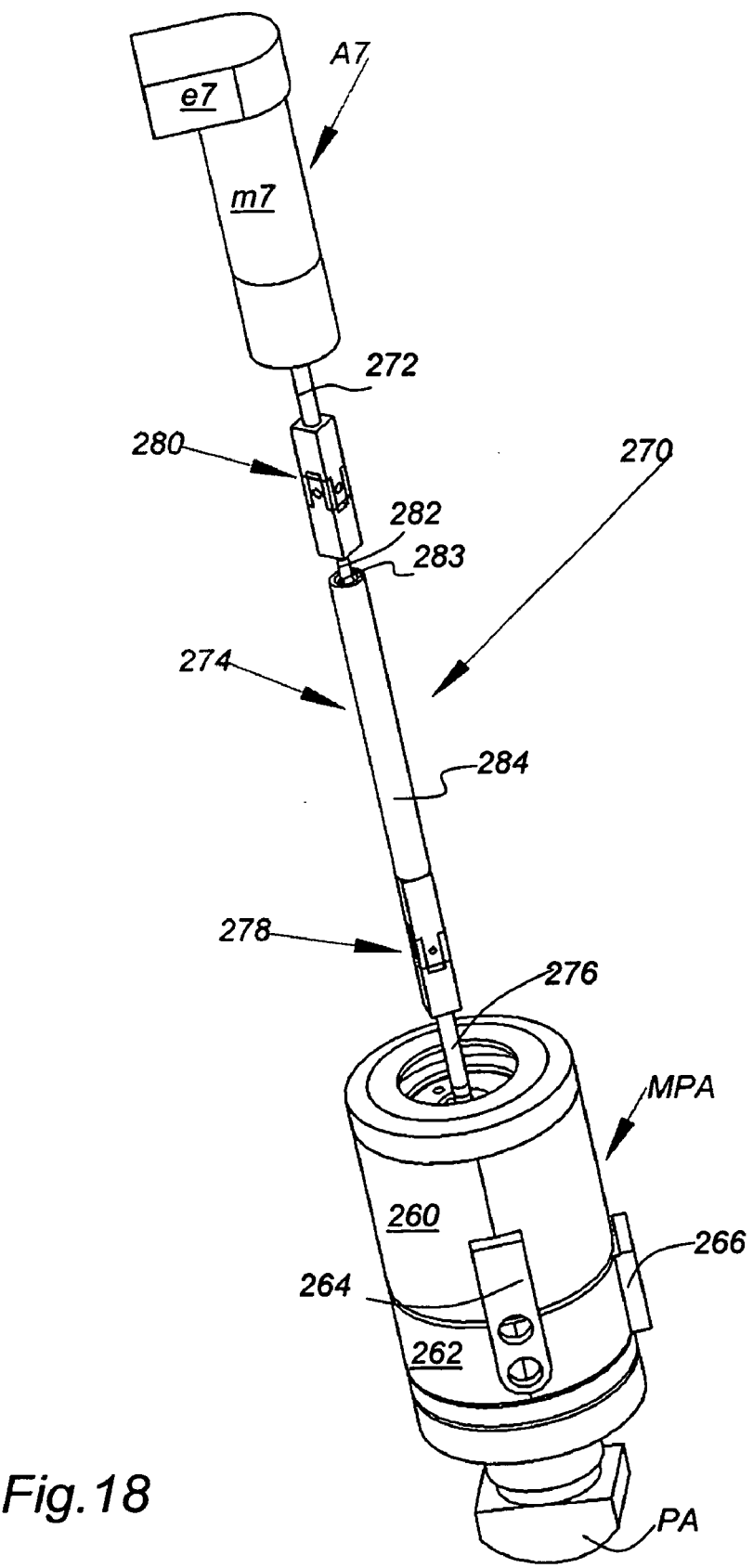
FIG. 18 is an isometric sectional view with parts omitted showing the drive arrangement for applying the third DoF to the end point.

The pantographs 216 and 218 operate in the same manner as the pantographs 16 and 18 described above in that as they are rotated with their respective shafts 228 and 230 (the plain of each pantograph is located in the plain of their respective shafts 228 and 230) to define a hemispherical motion of the point PA (which may for example indicate the surface of an ultrasound or palpation probe) about a remote center-of-motion (FCM) (see FIGS. 14, 15 and 16). In the FIG. 14 position the center-of-motion point FCM which is fixed relative to the base BA is shown aligned with the extreme free end PAF of the probe PA. It will be apparent that the axial extension of the probe relative to the moveable section MPA as will be described below and as schematically indicted in FIG. 14 by the arrow 235 will change the operation or movement of the probe PA for a given change in movement of the pantographs 216 and 218. It is preferred to position the center-of-motion point FCM so that axial movement of the probe PA may position the free end PAF on opposite sides of the center-of-motion point FCM.

As above indicated the rotatable shafts 228 and 230 are each is fixed to and positioned in fixed relation to the base BA via the frame 220. Mounted on the base BA are a pair of actuators $A_5$ and $A_6$ each of which may include its motor $m_5$ or $m_6$ and suitable encoders $e_5$ and $e_6$ that drives (or is driven by) and measures the rotation of its respective pantograph 216 and 218, respectively, via their respective shafts 228 and 230.

The motors $m_5$ or $m_6$ may have a gearbox for torque increase or speed reduction if desires and may also be directly coupled to shaft 228 and 230, respectively, in applications whereby motor closeness to the FCM is not of concern, however it is preferred to couple each of the motors $m_5$ or $m_6$ to its respective shaft 228 and 230 via the belt or cable drives 236 or 238, respectively.

The cable drive 236 and 238 are essentially the same except one 236 connects actuator $A_5$ with shaft 228 and the other 238 connects the actuator $A_6$ to the shaft 230. Thus only the drive 238 will be described with reference to FIGS. 13, 14, 16 and 17 it being understood that the drive 236 is essentially the same.

As shown the shaft 240 (see FIG. 16) of the motor $m_6$ has a pulley 242 mounted thereon and drives a cable 244 that passes over and is guided by suitable guide pulleys 246 some of which may also function as tensioners to tension the cable 244 and drives pulley 248. The pulley 248 has a companion pulley 250 fixed for rotation therewith and this pulley 250 drives a second cable 252 that drives the shaft 230 via pulley 254. A suitable tensioning pulley 256 may be provided, if desired.

As indicated the first degree of freedom is generated by motor $m_5$ and the cable drive that turns the pantograph 216 about the axis 232 of the shaft 228. The drive $m_6$ for second degree of freedom may but need not be idle when the first is operated but when activated rotates the second pantograph 218 with its shaft 230 i.e. about its axis 234.

A view of pantograph 218 is shown in FIG. 15. The lengths of the links in each pantograph 216 and 218 comply with the conventional length conditions used in most pantographs.

The first and second pantographs 216 and 218 as above indicated are located in two perpendicular planes. The pantographs 216 and 218 each connect to the device via their respective sleeves 260 and 262 i.e. the pantograph 218 has its link 264 remote from the shaft 230 connected to the sleeve 260 (see FIGS. 14, 15 and 16) and similarly the pantograph 216 has its link 266 remote from its shaft 228 fixed to the sleeve 262. The sleeves 260 and 262 are concentric with and may rotate relative to each other about the axis 212. Sleeves 260 and 262 are joined together via suitable ball bearings.

These two degrees defined by the pantographs 216 and 218 are decoupled.

The third DoF of the end point PA is provided by a shaft system 270 (see FIG. 18) formed by three shafts interconnected by a pair of inner universal joints namely a first inner universal 278 inter connecting shafts 276 and 284 and a second inner universal joint 280 interconnecting the shafts 272 and 282 (which is part of shaft 284). The shaft 272 is driven by actuator $A_7$ that normally will include a motor $m_7$ and an encoder $e_7$. The shaft 272 is in effect the motor shaft of the motor $m_7$ and the shaft 284 is made of an inner ball spline shaft 282 and outer ball spline nut 283 coupled together to permit relative axial movement while prohibiting relative rotational movement. Ball spline nut 283 is fixed to shaft 284 and thus connected to the first inner universal joint 278.

The shaft 276 coupled to the other side of the first inside universal joint is an output shaft that couples to the various modules (described below) that may interchangeably be received in the sleeves 260 and 262 of the mobile section MPA to drive same if required. The fourth DoF is provided by the mechanism shown in FIGS. 19, to 22. This fourth DoF is a rotation about the radius of the hemisphere created by the first two degrees of freedom and which is coaxial with the main axis 212 i.e. the rotational axis of the sleeves 260 and 262 is main axis 212. The roll or rotation motion is provided by the actuator $A_8$ that normally includes a grounded electric motor $m_8$ and an encoder $e_8$ The rotational motion from the electric motor $m_8$ is transmitted through a first cable or belt drive 290 composed of pulley 292, cable or belt 294 and pulley 296 that is attached to one side 300b of a second outside universal joint 300 that is concentric with the second inside universal joint 280. The other side 300a of universal joint 300 is coupled to an inner shaft 302 that telescopes within the concentric outer shaft 304 and these two shafts 302 and 304 are splined together by spline 306 and mating element 305 secured to shaft 304 (see FIGS. 20 and 22) so that the shafts 302 and 304 rotate together but permit relative axial movement there between in the same manner as the shafts 282 and 284. 300a and 300b are connected together by ring 300c, which also provides enough space to receive the inside universal joint 280.

The outside shaft 304 at its end remote from the universal joint 300 is fixed to one side 310b of a first outside universal joint 310 which is concentric with the first inside universal joint 278. The other side 310a of the universal joint 310, 310a is connected to 310b by ring 310c from one end, and to a pulley 314, from other end, to form the driving pulley for a second cable or belt drive system 316 wherein a belt or cable 318 passes over a plurality of properly positioned idle or guiding rollers 320 and a driven pulley 322 mounted on the sleeve 260 of the moveable section MPA for rotation about the axis 212 and fixed to a rotably driven module element to drive the module as will be described below. Pulley 314 is connected by a bearing to cup 259, which is in turn rigidly connected to 260.

A suitable cable or belt tensioning system 324 is provided for the belt or cable 318 and is formed by a pulley 324a mounted on an arm 324b whose position is adjustable to change the position of pulley 324a by means of nuts 324c.

Figure 19:
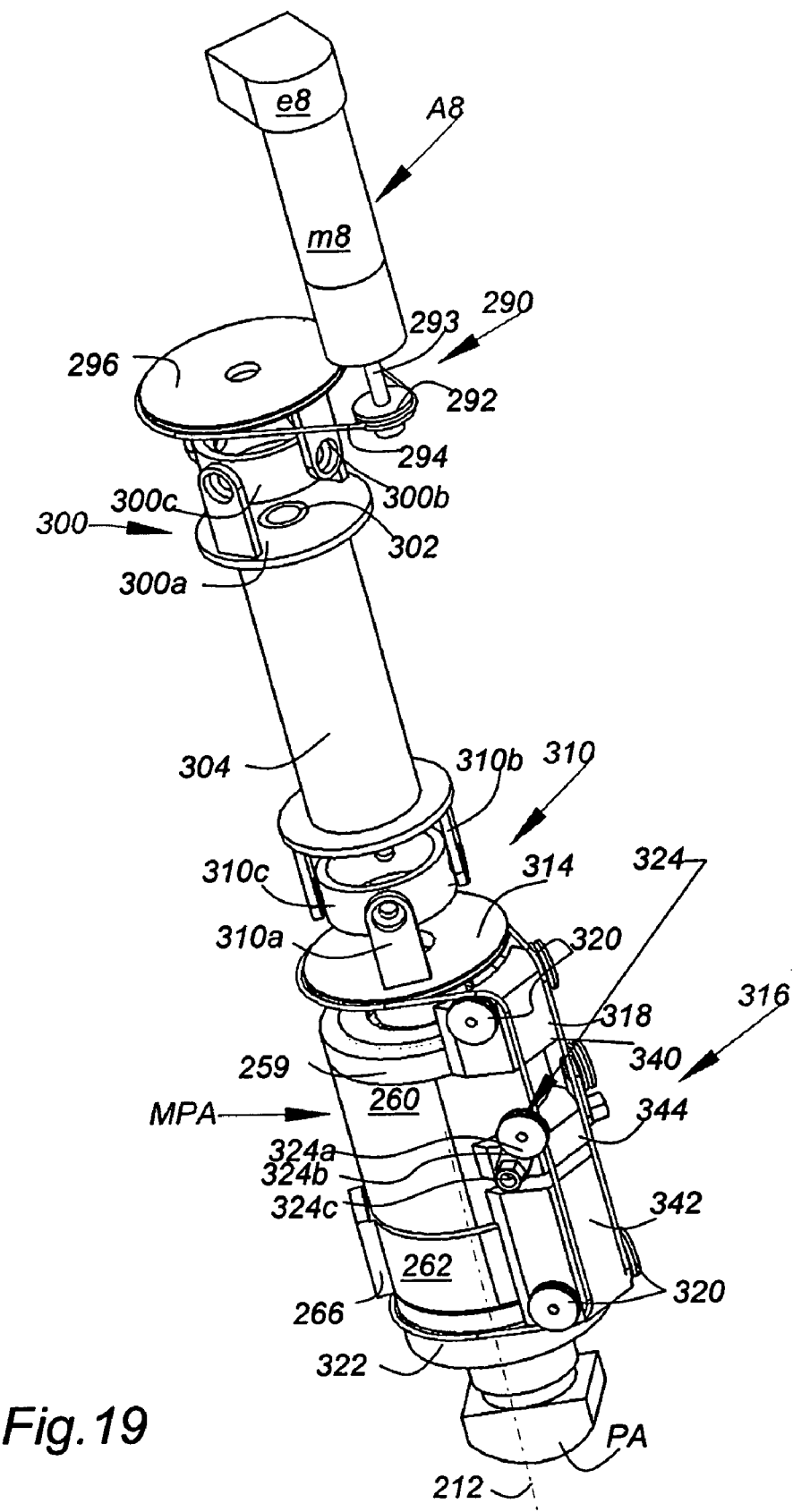
FIG. 19 is an isometric with parts omitted showing the drive arrangement for applying the fourth DoF to the end point.
Figure 20:
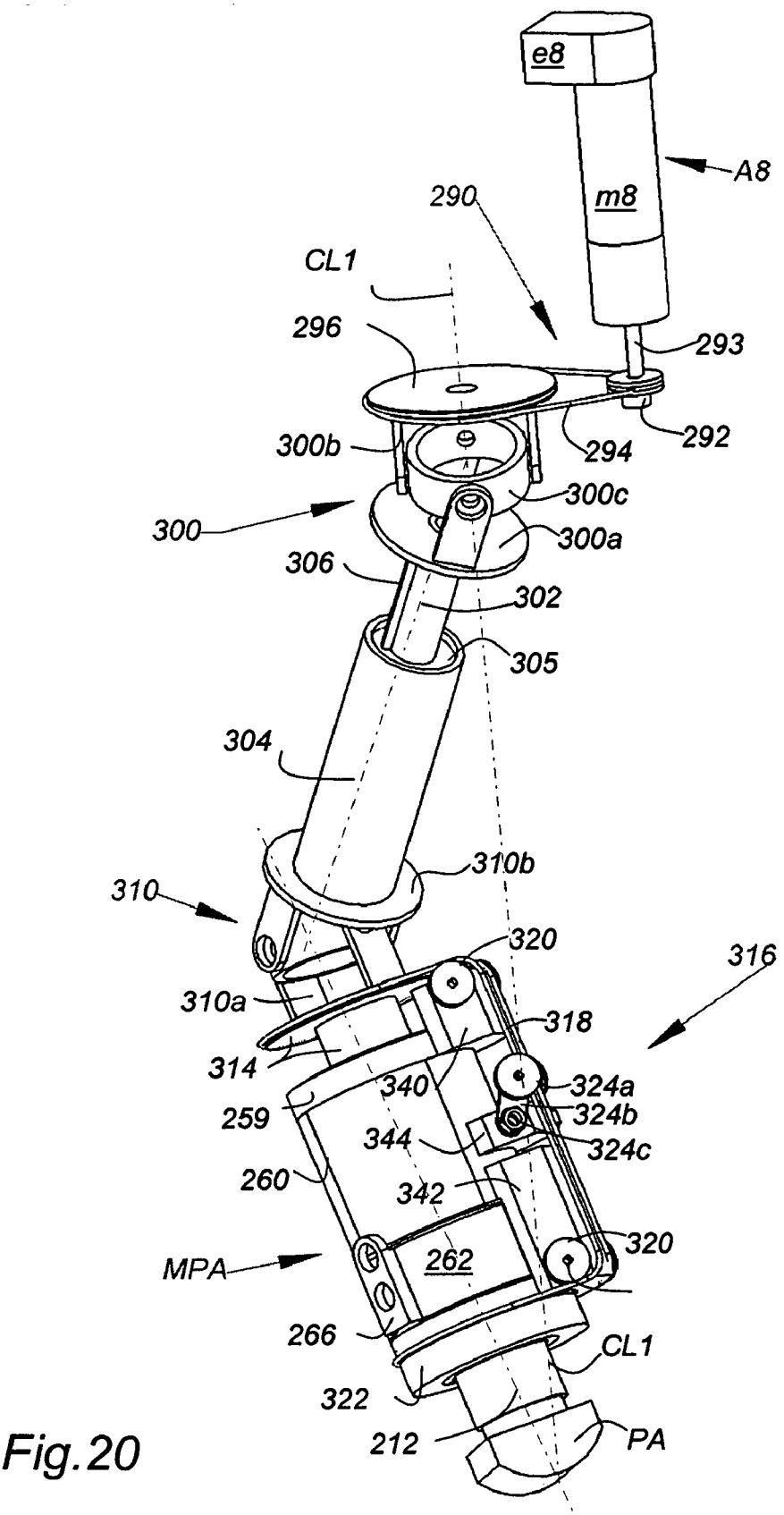
FIG. 20 is an isometric with parts omitted similar to FIG. 19 but showing the drive arrangement for applying the fourth DoF to the end point in a different orientation.

The guide rollers 320 and the tensioning systems 324 of the drive system 316 are mounted on the sleeve 260 of the pantograph through a series of modular blocks 340, 342 and 344 (FIGS. 19 and 20).

The first cable drive 290, drives the second outside universal joint 300 which in turn drives the first outside universal 310 via the telescoping shafts 302 and 304 interconnected by the spline 306 and the universal 310 that drives the cable system 316 thereby transmitting torque from a fixed rotation source $A_8$ to a moving joint in space in any orientation (see FIGS. 19, and 20). This allows a module (described below) mounted in the sleeves 260 and 262 of the moveable portion or section MPA to be rotatably driven and to idly follow the movement of the moveable portion MPA by the first two DoF for the moveable section MPA so that torques is transmitted to drive the fourth DoF of the wrist 10A.

Figure 21:
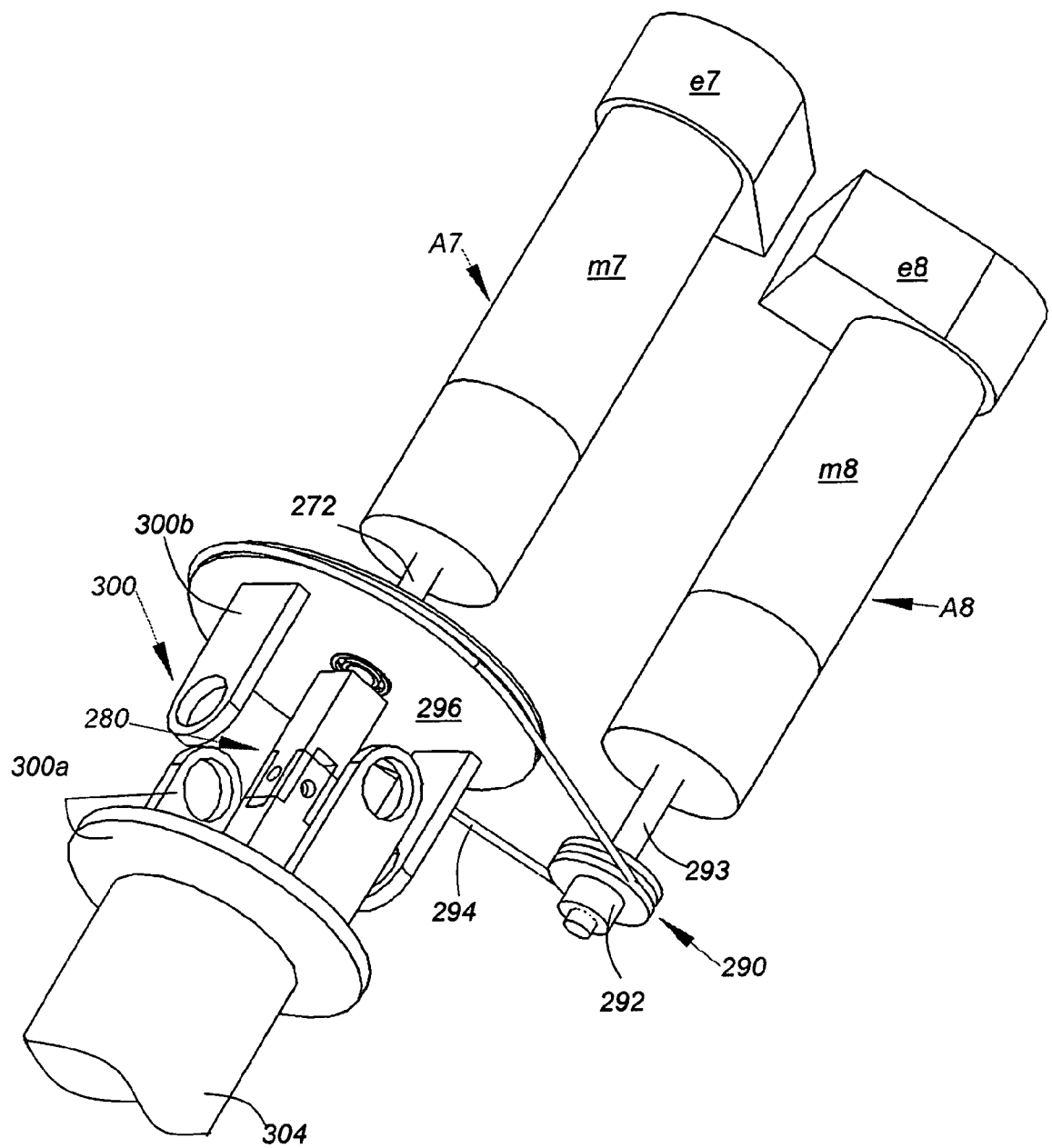
FIG. 21 is an isometric view with parts omitted showing the base end of the drive arrangement for applying the third and fourth DoF to the end point of the wrist.
Figure 22:
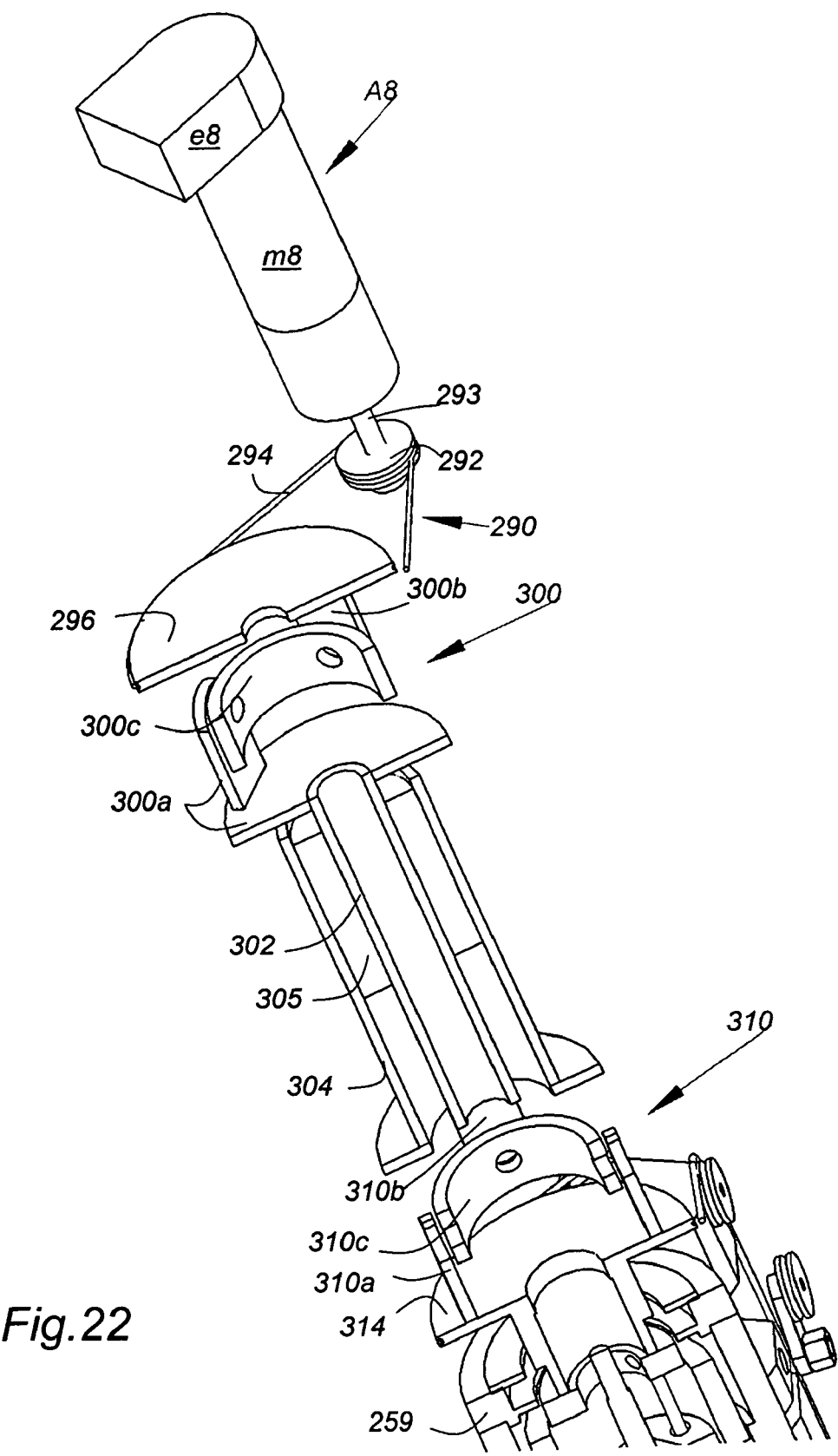
FIG. 22 is an isometric sectional view with parts omitted showing part of the drive system for the fourth degree of freedom of the wrist.

FIG. 21 shows the relationship of the actuators $A_7$ and $A_8$ and their respective driving relationships with the second inside universal 280 and second outside universal 300, respectively and the concentric relationship of the two second universals 280 and 300 that are mounted with respect to each other by a ball bearing. As above indicated the two first universals namely first inside universal 278 and first outside universal 310 have a similar concentric relationship to that shown in FIG. 21 for the second inside 280 and second outside 300 universals and above described for the inside and outside universals 40 and 90 of the device 10 described above.

The wrist 10A may include more than one module designed so that the modules can be easily substituted for one another i.e. quickly attached and/or detached in the sleeves 260 and/or 262 of the moveable section MPA.

The wrist 10A in the illustrated embodiments is provided with two interchangeable modules 500 and 600 each of which may be quickly attached and detached (see FIGS. 23 to 26).

Figure 23:
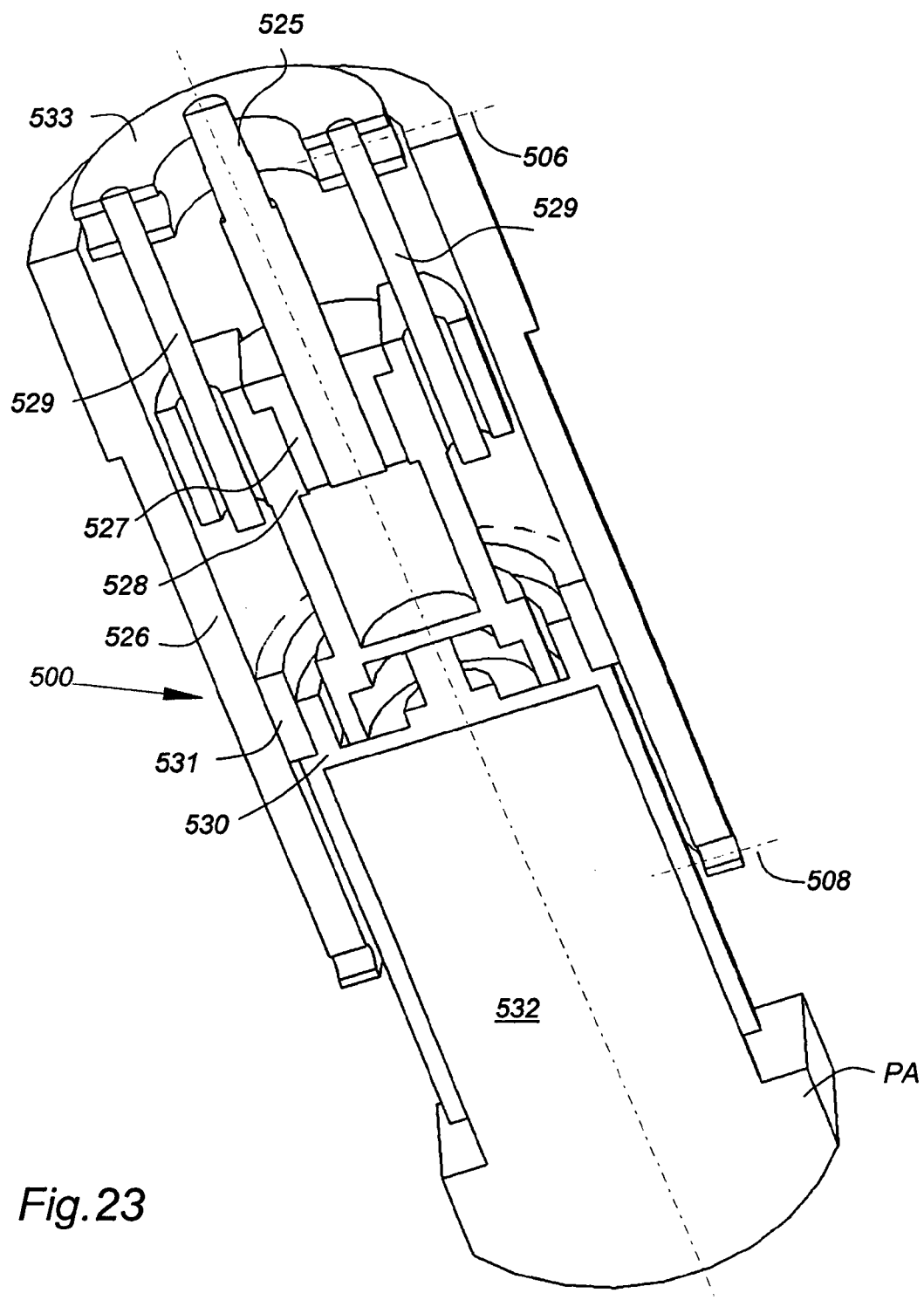
FIG. 23 is an isometric sectional illustration with parts omitted showing a wrist module (probing assembly) for mounting in the wrist assembly for applying four degrees of freedom.
Figure 24:
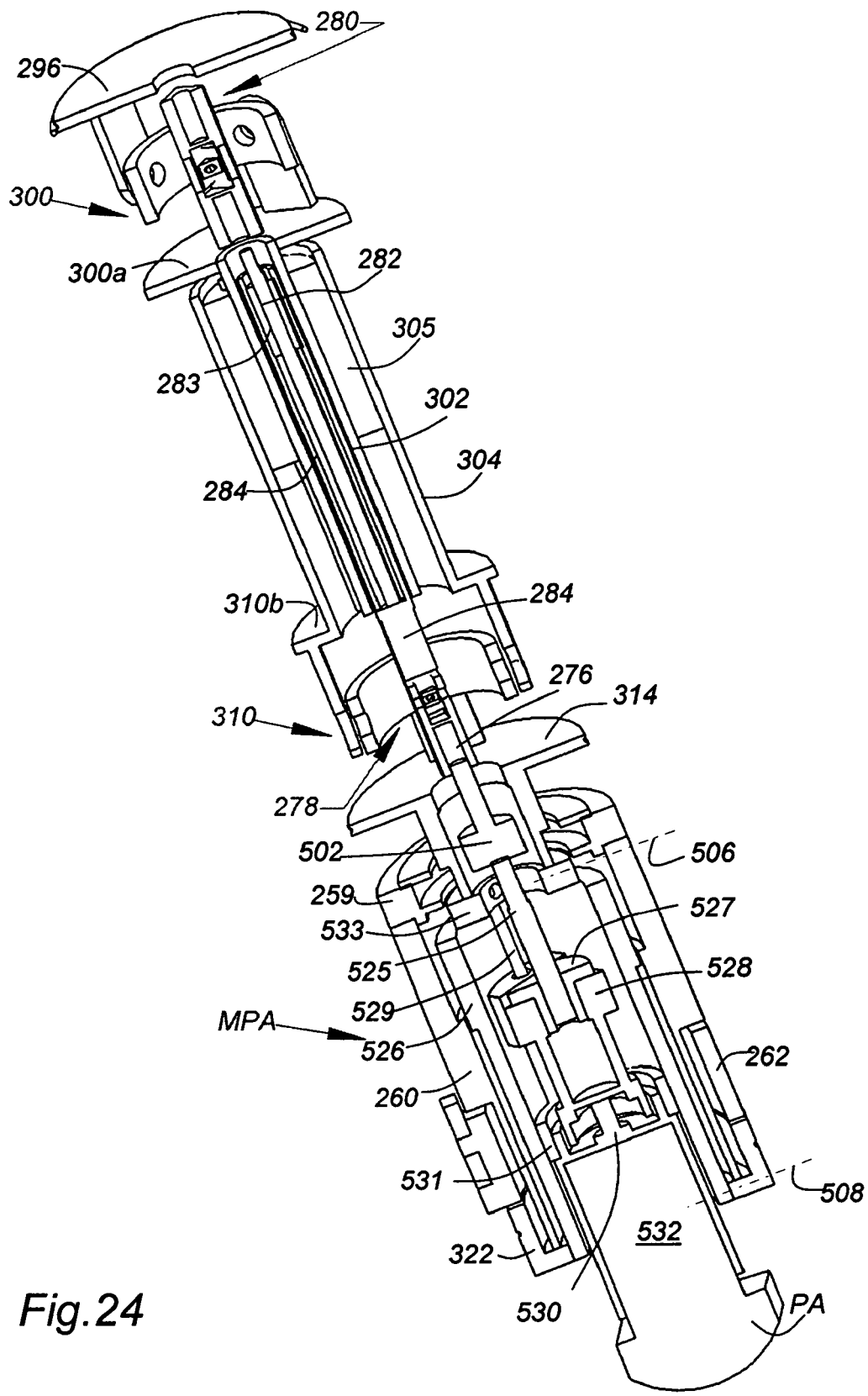
FIG. 24 shows the detailed isometric sectional illustration with parts omitted showing a wrist module (probing assembly) for mounting in the wrist assembly for applying four degrees of freedom mounted in the wrist assembly.
Figure 25:
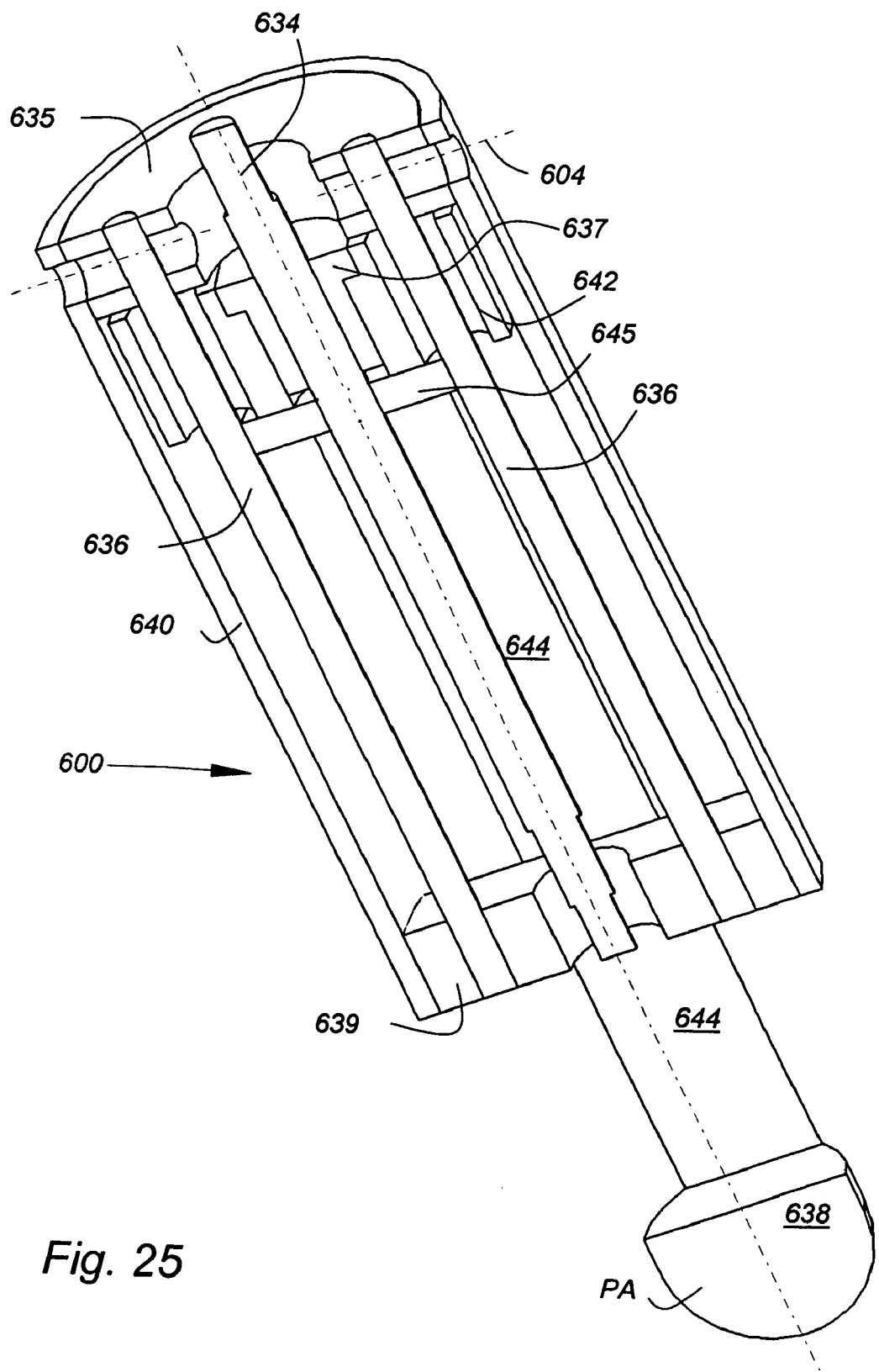
FIG. 25 is an isometric sectional illustration with parts omitted showing a wrist module (probing assembly) for mounting in the wrist assembly for applying only three DoF.
Figure 26:
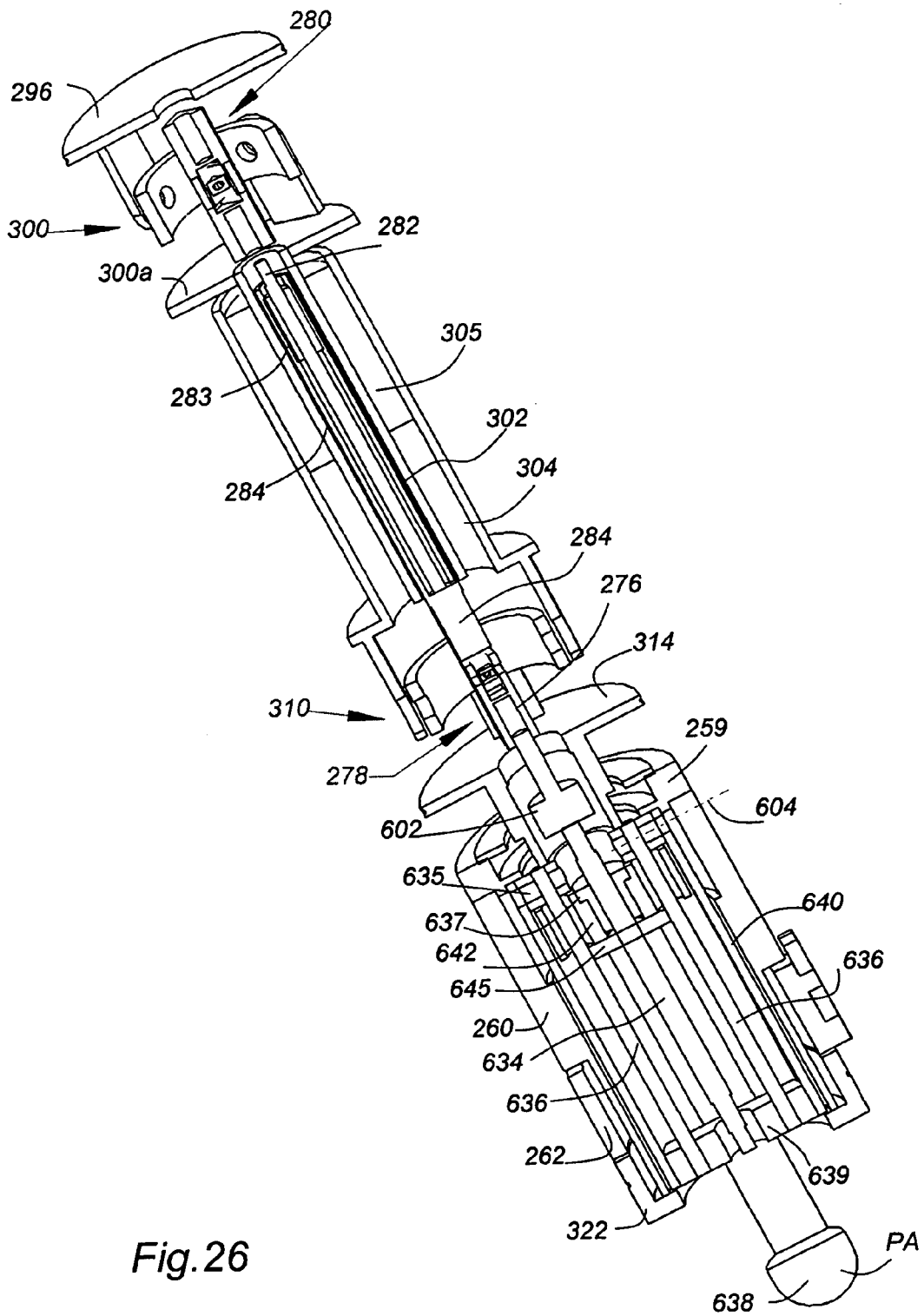
FIG. 26 is an isometric sectional illustration with parts omitted showing a wrist module (probing assembly) for mounting in the wrist assembly for applying three DoF mounted in the wrist assembly.

The first module 500 has two degrees of freedom (FIGS. 23 and 24). This module 500 transmits the rotation of pulley 314 to the working probe 532 forming the end point PA. It also converts motion of the fourth degree of freedom i.e. the rotation of shaft 276 into the sliding motion of the working probe 532.

The module 500 has an outside housing 526 that is received in and detachably mounted in the moveable section MPA in any suitable manner. In the arrangement illustrated in FIG. 24 a retractable coupling pin pins the module in position and functions to prevent rotation of a slider 528 as will be described below.

The shaft 276 is coupled to a ball screw drive shaft 525 of the module 500 via a self-aligning coupling 502 and drives a ball screw's nut 527 fixed to a slider 528 (see FIG. 24). Linear guides 529 are fixed to end support 533, and prevent rotation of the nut 527 with the shaft 525 while permitting relative axial sliding movement between the slider 528 and the end support 533. The end support 533 is fixed to sleeve 260 of the pantograph 218 by a coupling pin schematically indicated at 506 to prevent rotation of the end support 533 and thereby through guides 529 prevent rotation of the slider 528. The ball screw drive shaft 525 is mounted on end support 533 by a ball bearings (not shown). The linear guides 529 are connected to slider 528 by two linear ball bushing (not illustrated).

Slider 528 is mounted on connector 530 via a decoupling ball bearing (not shown). Thereby to decouple the rotating motion of connector 530 imparted by the drive 316 from sliding motion of the slider 528 so that the module can achieve three modes of motion (rotational, sliding and spiral as needed).

The connector 530 also connects the working probe 532 with a ball spline nut 531 that prevents relative rotational movement of the probe PA and the housing 526 while permitting relative axial movement parallel to axis 212 there between. The housing 526 is connected to pulley 322 by coupling pin schematically indicated at 508 and receives it rotary motion from pulley 322 driven via drive 316 as above described. Obviously the rotary motion imparted to the housing 526 is transferred to the probe PA by the spline nut 531.

Probe 532 is preferably attached to the connector 530 through an off-the-shelf six axes force/torque sensor (not shown).

When the module 500 is in operative position (see FIG. 24), ball screw's shaft 525 is connected to the shaft 276 by off-the-shelf self aligning coupling 502 and the housing 526 of the module 500 (or 600) is mounted within the outer housing formed by sleeve 260 on suitable bearings (not shown) and pinned in place by pin 506 (and 508) as described above.

This module in combination with the four degrees of freedom allows the wrist to orient and palpate.

The second module 600 (see FIGS. 25 and 26) converts the rotary motion of the shaft 276 into a sliding motion of the probe 638 (probe PA) along the radius of the hemisphere created by the action of the pantographs 216 and 218 to provide a wrist with three degrees of freedom.

This module 600 has housing 640 in which the inner elements of the module 600 are contained.

A drive shaft or ball screw 634 of this module 600 is coupled to the shaft 276 via a self aligning coupling 602 (see FIG. 26 similar to the coupling 502 described above) and rotation of the ball screw shaft 634, tends to rotate nut 637, which is connected rigidly to slider 642 and which in turn is connected via extension 644 to the probing device 638 forming the end point PA. Slider 642 is restrained from rotation by the linear guides 636 (two shown) connected to the slider 642 by sets of linear ball bushings (not shown) that permit relative axial movement between the guides 636 and the slider 642. Therefore, rotation of the ball screw shaft 634 causes the nut 637 and slider 642 moves along the ball screw 634.

The linear guides 536 are rigidly connected to plates 635 and 639, which are in turn fixed to the housing 640. The housing 640 is connected to sleeve 260 by coupling pin 604. This module does not receive any motion from pulley 322.

Figure 27:
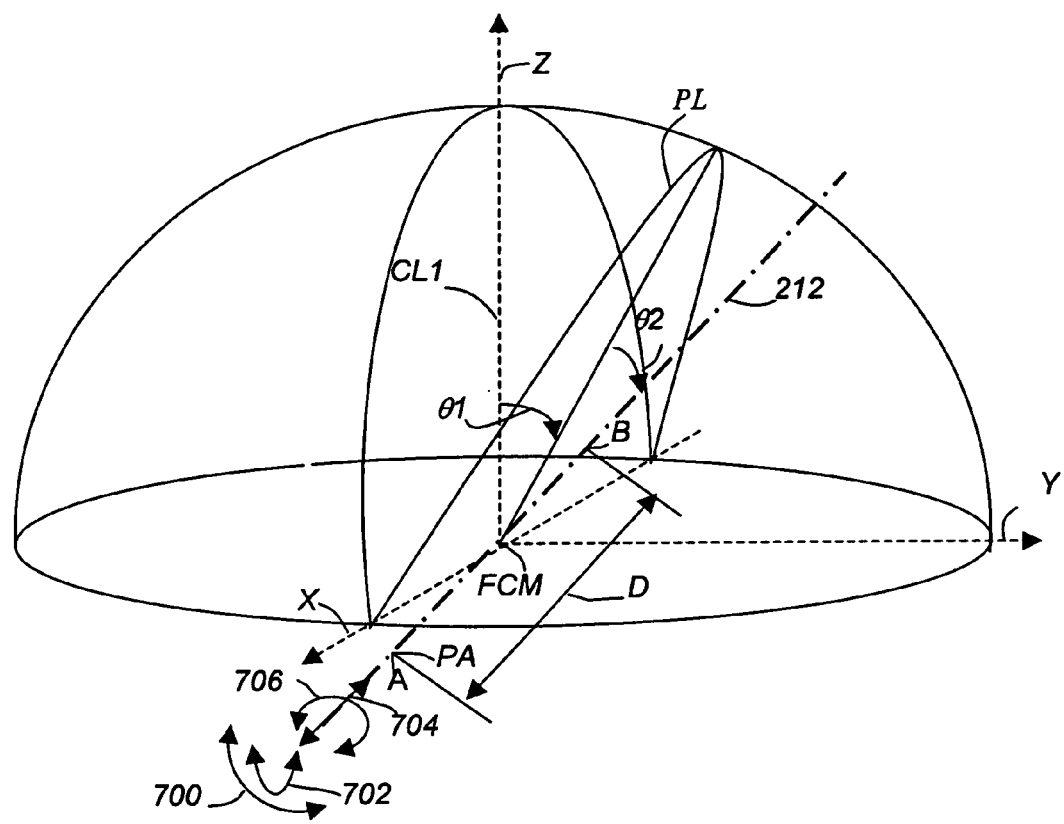
FIG. 27 is a schematic illustration similar to FIG. 11 but showing the movements of the probe or end point of the embodiment of FIGS. 12 to 26.

In combination with the first three degrees of freedom, this module is able to perform the palpation action in any orientation and reports on all arising forces from palpation. FIG. 27 schematically indicates the action of the wrist 10A. As illustrated the angle $\theta_1$ and $\theta_2$ (which are essentially equivalent to the angles $\beta_1$ and $\beta_2$ of the embodiment of FIGS. 2 to 11) between the datum centerline CL1 for the moveable section MPA and the actual central or main axis 212 at the center of movement FCM measured in the planes relative to the X and Y axes, respectively, in the same manner as angles $\beta_1$ and $\beta$2. These angles $\theta_1$ and $\theta_2$ are determined by the action of the two pantographs 216 and 218 in the same manner as the pantographs 16 and 18 determined the angles $\beta_1$ and $\beta_2$ as described above for the haptic device 10. The end point PA may be moved by the pantographs 216 and 218 in two mutually perpendicular directions as indicated by the arrows 700 and 702 and depending on the module used i.e. module 500 or 600 may be moved both axially as indicated by the arrow 704 and rotated around the axis 212 as indicated by the arrow 706 when the module 500 is used, or when the module 600 is used there is no movement as schematically indicated by the arrow 706.

The device 10A may be set so that axial travel of the probe PA along the axis 212 between the points A and B as indicated by the dimension D may set so that one extremity of travel point A is on one side of the center FCM and the opposite extremity point B is on the opposite side of center FCM along the axis 212. It will be apparent that movement of the end point PA moves on a hemisphere based on the position of the end point PA relative to the point FCM and will have having a radius measure along axis 212 from point PA to the point FCM. When the point PA is to the left of the point FCM in FIG. 27 the point PA moves in a convex pattern, but when PA is on the opposite side of the point FCM it moves in a concave pattern when the pantographs 216 and 218 are manipulated.

If desired the location of the center FCM may be made adjustable by having the lengths of the links of the pantographs 216 and 218 connecting the pantographs to the MPA to be axially adjustable.

Having described the invention, modifications will be evident to those skilled in the art without departing from the scope of the invention as defined in the appended claims.

We claim:

1. A hand controller or wrist device comprising a base and a moveable portion moveable relative to said base, said moveable portion having a main longitudinal axis and an end point, a pair of pantographs each formed by a plurality of pivotably interconnected links arranged for pivotal movement in a plane, said planes being mutually perpendicular, means for pivotably mounting each said pantograph adjacent to one of its ends for rotational movement on its pivotal axis relative to said base in a direction substantially perpendicular to its plane and coupling means connecting each of said pantographs adjacent to its end remote from its one end to move said end point in a hemispherical path about a center point when said pantographs are pivoted on their said means for pivotably mounting, said pantographs defining a first and a second degree of freedom of said end point;

said center point being defined by the intersection of said pivotal axes and said main longitudinal axis, an inner universal joint, said inner universal interconnecting a first inside element and a second inside element forming a pair of inside elements that define a third degree of freedom of said end point, said first of said inside elements including a pair of portions and means for translating axial movement substantially parallel to said main axis of one of said pair portions of said first inner element to rotational movement of a second portion of said pair of portions of said first inner element and vice versa while permitting relative rotational movement between said one and said second portions, said end point being connected to said one portion of said one of said second pair of elements and, means for mounting said second inside element for rotation about it axis relative to said base;

said coupling means connecting said pantographs to said one portion while permitting movement of said one portion relative to said pantographs.

2. A hand controller or wrist as defined in claim 1 further comprising an outside universal joint concentric with said inside universal joint combines with said inside universal joint to provide a pair of concentric universal joints, said outside universal joint interconnecting a first outside element and second outside element that form a pair of outside elements; and means coupling said first outside element to said one portion of said first inside element to prohibit relative rotational movement while permitting relative axial movement between said one portion and said first outside element.

3. A hand controller or wrist as defined in claim 2 wherein said pair of outside elements defines a fourth degree of freedom of said end point.

4. A hand controller or wrist as defined in claim 2 wherein said device s a controller and said center point and said inner universal joint pivot point are in the same location.

5. A hand controller or wrist as defined in claim 4 further comprising a separate actuator for each of said degrees of freedom and each said actuator is supported on said base.

6. A hand controller or wrist as defined in claim 5 wherein said device is a controller and said actuators provide force feedback to said end point in each of said degrees of freedom and said center point is defined by the intersection of said pivotal axes and said main longitudinal axis and said end point is moved about said center point by operation said degrees of freedom.

7. A hand controller or wrist as defined in claim 6 wherein said actuator for said third degree of freedom is coupled to said second inside element and through said inner universal joint to said second portion of said first inside element.

8. A hand controller or wrist as defined in claim 7 wherein said means for translating axial movement to rotational movement and vice versa include a belt type drive which includes a pulley formed by a pulley that rotates with said second portion and a belt having a path of travel parallel to said axial movement and connected to said one portion so that movement of said belt moves said one portion substantially axially.

9. A hand controller or wrist as defined in claim 6 wherein said actuator for said fourth degree of freedom includes a belt type drive coupling with said second outside element of said pair of outside elements and through said outside universal joint with said first outside element of said pair of outside elements.

10. A hand controller or wrist as defined in claim 7 wherein said actuator for said fourth degree of freedom includes a belt type drive coupling with said second outside element of said pair of outside elements and through said outside universal joint with said first outside element of said pair of outside elements.

11. A hand controller or wrist as defined in claim 8 wherein said actuator for said fourth degree of freedom includes a belt type drive coupling with said second outside element of said pair of outside elements and through said outside universal joint with said first outside element of said pair of outside elements.

12. A hand controller or wrist as defined in claim 1 further comprising separate actuators for each of said degrees of freedom.

13. A hand controller or wrist as defined in claim 10 wherein said device is a wrist and said actuators drive said end point in each of said degrees of freedom.

14. A hand controller or wrist as defined in claim 13 wherein said means for mounting said second inside element for rotation about it axis includes a second inside universal joint, said second inside universal joint coupled on one side to said second inside element and its other side is rotatably mounted on said base on said base.

15. A hand controller or wrist as defined in claim 14 further comprising an outside universal joint concentric with said inside universal joint combines with said inside universal joint to provide a pair of concentric universal joints, said outside universal joint interconnecting a first outside element and second outside element that form a pair of outside elements; and means coupling said first outside element to said one portion of said first inside element to prohibit relative rotational movement while permitting relative axial movement between said one portion and said first outside element and wherein a second outside universal joint concentric with said second inside universal joint combines with said second inside universal joint to provide a second pair of concentric universal joints, said second outside universal joint coupled on one side to said second outside element and its other side is rotatably mounted on said base.

16. A hand controller or wrist as defined in claim 15 wherein said actuator for each of said first and second degrees of freedom includes a belt type drive drivingly interconnecting its respective said means for pivotably mounting with its actuator.

17. A hand controller or wrist as defined in claim 16 wherein said actuator for said third degree of freedom is coupled to one side of said second inside universal joint and another side of said second inner universal joint is connected to said second inside element and through said inner universal joint to said second portion of said first inside element.

18. A hand controller or wrist as defined in claim 16 wherein said actuator for said fourth degree of freedom includes a belt type drive coupling with one side of said first outside universal joint.

19. A hand controller or wrist as defined in claim 16 wherein said means for translating axial movement to rotational movement and vice versa includes a worm type gear.

20. A hand controller or wrist as defined in claim 16 wherein said one portion is a module.

* * * * *